(12) United States Patent
Hoshino

(10) Patent No.: US 12,150,747 B2
(45) Date of Patent: Nov. 26, 2024

(54) MAGNETIC RESONANCE IMAGING APPARATUS AND METHOD OF CONTROLLING THE SAME

(71) Applicant: FUJIFILM Corporation, Tokyo (JP)

(72) Inventor: Yusuke Hoshino, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 8 days.

(21) Appl. No.: 17/335,133

(22) Filed: Jun. 1, 2021

(65) Prior Publication Data

US 2022/0015661 A1 Jan. 20, 2022

(30) Foreign Application Priority Data

Jul. 17, 2020 (JP) ................................. 2020-123139

(51) Int. Cl.
*A61B 5/055* (2006.01)
*G01R 33/48* (2006.01)
(Continued)

(52) U.S. Cl.
CPC .......... *A61B 5/055* (2013.01); *G01R 33/4818* (2013.01); *G01R 33/543* (2013.01); *G01R 33/5615* (2013.01)

(58) Field of Classification Search
CPC .. A61B 5/055; A61B 5/0033; G01R 33/4818; G01R 33/543; G01R 33/5615;
(Continued)

(56) References Cited

U.S. PATENT DOCUMENTS

2010/0152568 A1 6/2010 Katsutoshi
2013/0021030 A1* 1/2013 Zuehlsdorff ........... G01R 33/48
324/309

(Continued)

FOREIGN PATENT DOCUMENTS

CN 101779957 7/2010
CN 104714199 A 6/2015
(Continued)

OTHER PUBLICATIONS

Chinese Office Action received in corresponding Chinese Application No. 202110310713.8 dated May 20, 2023.
(Continued)

*Primary Examiner* — Alexei Bykhovski
(74) *Attorney, Agent, or Firm* — MATTINGLY & MALUR, PC

(57) ABSTRACT

Even when imaging is aborted, data collected so far is utilized in image reconstruction, thereby enhancing examination efficiency. A certain priority imaging data available for image reconstruction by a fast-imaging method is determined, when collecting k-space data according to a predetermined imaging method. If collection of the certain priority imaging data is completed when imaging is aborted, imaging reconstruction is executed using the priority imaging data. The priority imaging data is determined based on a relationship between the imaging method under execution, and the fast-imaging method underlying determination of the priority imaging data.

14 Claims, 21 Drawing Sheets

(51) Int. Cl.
*G01R 33/54* (2006.01)
*G01R 33/561* (2006.01)

(58) Field of Classification Search
CPC .............. G01R 33/4824; G01R 33/561; G01R 33/5617; G01R 33/5611
See application file for complete search history.

(56) References Cited

U.S. PATENT DOCUMENTS

| | | | |
|---|---|---|---|
| 2015/0276908 | A1* | 10/2015 | Takeshima ......... G01R 33/5611 324/322 |
| 2017/0184694 | A1 | 6/2017 | Guobin et al. |
| 2018/0204358 | A1 | 7/2018 | Hongyu et al. |
| 2019/0094320 | A1* | 3/2019 | Bannae ............. G01R 33/4822 |
| 2019/0347834 | A1 | 11/2019 | Masaaki et al. |
| 2021/0278493 | A1* | 9/2021 | Kondo ............. G01R 33/56554 |
| 2022/0146614 | A1* | 5/2022 | Beck ................. G01R 33/5611 |

FOREIGN PATENT DOCUMENTS

| | | | |
|---|---|---|---|
| CN | 107865659 | A | 4/2018 |
| JP | 02-243133 | A | 9/1990 |
| JP | 06-70900 | A | 3/1994 |
| JP | 3510901 | B2 | 3/2004 |
| JP | 2010-162332 | A | 7/2010 |
| JP | 2018130142 | A * | 8/2018 |
| NO | 2010/116772 | A1 | 10/2010 |
| WO | 2016/170863 | A1 | 10/2016 |
| WO | 2018/051649 | A1 | 3/2018 |

OTHER PUBLICATIONS

Chinese Office Action received in corresponding Chinese Application No. 202110310713.8 dated Sep. 13, 2023.
Japanese Office Action received in corresponding Japanese Application No. 2020-123139 dated Nov. 28, 2023.
Chinese Office Action received in corresponding Chinese Application No. 202110310713.8 dated Jan. 24, 2024.

* cited by examiner

MAGNETIC RESONANCE IMAGING APPARATUS AND METHOD OF CONTROLLING THE SAME

INCORPORATION BY REFERENCE

The present application claims priority from Japanese patent application JP-2020-123139 filed on Jul. 17, 2020, the content of which is hereby incorporated by reference into this application.

BACKGROUND OF THE INVENTION

Field of the Invention

The present invention relates to a magnetic resonance imaging apparatus (hereinafter, referred to as MRI apparatus), in particular to a method of controlling the MRI apparatus to control priority of signal acquisition.

Description of the Related Art

An MRI apparatus measures a nuclear magnetic resonance (hereinafter, referred to as NMR) signal caused by NMR phenomenon in nuclei constituting tissues of a subject, for example, a human body, and generates an image two-dimensionally or three-dimensionally.

In imaging, the NMR signal is provided with phase encoding that varies depending on a gradient magnetic field, along with frequency encoding, then the NMR signal is repeatedly measured at a repetition time called TR, and stored in data space called k-space. The measured NMR signals are subjected to two-dimensional or three-dimensional Fourier transform and reconstructed into an image.

The imaging method differs depending on the purpose of diagnosis, a target site, and so on, but basically, the imaging method measures all data points in k-space, corresponding to the matrix size of the k-space, in order to obtain a high-resolution image without artifacts. For this measurement, there has been developed a fast-imaging technique for measuring data in the k-space, with decimating data. This imaging method, called parallel imaging, uses a sensitivity distribution of a receiving coil to create an image without artifacts. Also there is known another fast-imaging technique called iterative reconstruction such as compressed sensing. The iterative reconstruction such as the compressive sensing is a reconstruction method that measures k-space sparsely and utilizes its sparsity to reduce noise, and an image can be restored with less data than usual.

Upon imaging, an imaging method suitable for the purpose is selected from the various techniques described above, and a pulse sequence and imaging parameters are provided for executing the imaging method. The imaging time varies depending on the imaging method, and when obtaining a three-dimensional image, the time of approximately 5 to 10 minutes is required even when using the above-described fast imaging technique. If the subject body moves during this time, it may cause a large deterioration in an image quality, and thus, there have been proposed various methods for preventing influence of such body motion.

SUMMARY OF THE INVENTION

Technical Problem

In the case where the subject has moved with changing its position during the imaging, or in the case where the subject feels sick to continue the examination and the imaging is aborted, conventional body motion control techniques cannot address such problems. Therefore, it has been necessary to wait for recovery of the subject or restoring the posture, and then the subject is rearranged in the imaging space to perform re-imaging to capture data once again. Therefore, in addition to the problem of lowering the examination efficiency due to the aborted imaging, there is a problem that the data collected so far is discarded and wasted. The imaging may also be paused due to a reason on the examiner side, and this also cause a similar problem.

In Japanese Patent No. 3510901 (hereinafter, referred to as Patent Document 1), there is described that when imaging is aborted, if a half or more data of the k-space data has been successfully acquired, an image can be reconstructed by estimation by a half-scan method for estimating the remaining data. This method, however, can be applied only to the imaging that measures the data continuously from the edge of k-space.

Solution to Problem

The present invention is directed to enhancing examination efficiency by utilizing data collected so far in reconstructing an image, even when imaging is aborted.

In an aspect of the present invention, when collecting k-space data according to a predetermined imaging method, there is provided a certain amount of priority imaging data that is available for image reconstruction by a fast-imaging method. If collection of the certain amount of priority imaging data is completed at the time of aborted imaging, the image reconstruction is executed by utilizing the collected priority imaging data. The priority imaging data is determined based on a relationship between the imaging method under execution, and the fast-imaging method underlying determination of the priority imaging data.

That is, an MRI apparatus according to an aspect of the present invention comprises, a measuring unit configured to collect k-space data made up of a plurality of nuclear magnetic resonance signals in accordance with a predetermined imaging method, an image generator configured to generate an image using the k-space data collected by the measuring unit, and a control unit configured to control operations of the measuring unit and the image generator, wherein the control unit includes a priority imaging data determiner configured to determine as priority imaging data, imaging data that is available for image reconstruction according to a fast imaging method, among the k-space data, and controls a signal acquisition order so that the measuring unit collects the priority imaging data in advance.

A method of controlling an MRI apparatus according to an aspect of the present invention is a method of the MRI apparatus comprising a measuring unit configured to collect k-space data made up of a plurality of nuclear magnetic resonance signals in accordance with a predetermined imaging method, an image generator configured to generate an image using the k-space data collected by the measuring unit, and a control unit configured to control operations of the measuring unit and the image generator, and the method comprises, determining priority imaging data that is collected in advance among the k-space data, in accordance with the predetermined imaging method, controlling the measuring unit to collect the k-space data starting from the priority imaging data, and controlling the image generator to perform image reconstruction based on a fast imaging method by utilizing the priority imaging data, when signal acquisition is aborted by the measuring unit after collection of the priority imaging data is completed.

According to the present invention, some of the k-space data is determined as priority imaging data that is available for the image reconstruction according to the fast-imaging method, and the priority imaging data is collected in advance. Therefore, if the priority imaging data has already been collected by the time the imaging is aborted, it is possible to generate an image using the priority imaging data and this allows utilization of the acquired data. In addition, even if there remains data to be discarded, it is possible to reduce waste as much as possible. If the image generated according to the fast-imaging method has an image quality that meets the purpose of imaging, it is also possible to omit re-imaging, thereby preventing deterioration of the examination efficiency.

BRIEF DESCRIPTION OF THE DRAWINGS

FIG. 2A is a flow diagram showing steps until determining the signal acquisition order, and FIG. 2B is a flow diagram showing a control process at the time of imaging;

DETAILED DESCRIPTION OF THE PREFERRED EMBODIMENTS

There will now be described embodiments of an MRI apparatus according to the present invention, with reference to the accompanying drawings.

Figure 1:
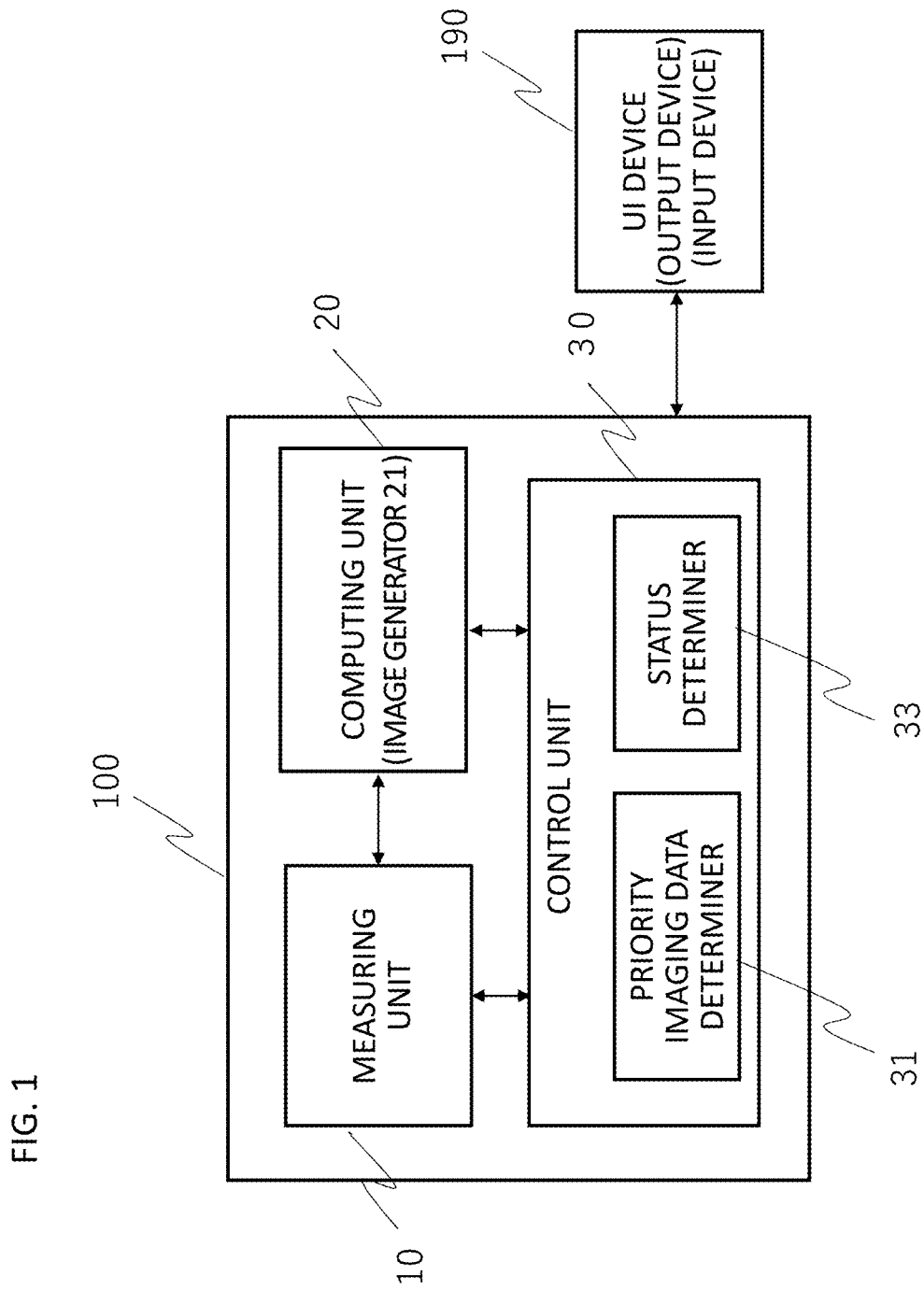
FIG. 1 is a functional block diagram of an MRI apparatus.

FIG. 1 is a diagram showing a schematic configuration of the MRI apparatus 100 having features of the present invention, and the MRI apparatus 100 comprises a measuring unit 10 configured to collect k-space data made up of a plurality of nuclear magnetic resonance signals in accordance with a predetermined imaging sequence, an computing unit 20 configured to perform an operation such as image reconstruction using the k-space data collected by the measuring unit, a control unit 30 configured to control the operations of the measuring unit 10 and the computing unit 20. The MRI apparatus 100 further includes a UI device 190 to interact with a user. Through the UI device 190, the user can set imaging conditions, or check the image acquired by the MRI apparatus 100.

The measuring unit 10, as described in detail later, has the same configuration as a publicly known MRI apparatus, comprising a static magnetic field generator, a gradient magnetic field generator, an RF magnetic field generator, a receiving unit for receiving an NMR signal, and a sequencer for controlling the units above according to a predetermined pulse sequence, and so on. The measuring unit measures the NMR signal from a test object (subject) placed in a static magnetic field generated by the static magnetic field generator, and collects measurement data (k-space data) for image reconstruction. Collection of the k-space data is performed under the control of the control unit 30, and priority imaging data set by the control unit 30 is measured in advance.

The computing unit 20 includes an image generator 21 that performs computations on the k-space data, such as the Fourier transform, a computation based on parallel imaging, a computation based on iterative reconstruction such as compressed sensing, and further a computation between images, to generate a tomographic image of the subject and a desired calculated image.

The control unit 30 controls measurement of the NMR signal performed by the measuring unit 10 via the sequencer, and controls the image generator 21 so as to generate an image according to a predetermined data collection method and the timing of the measurement. The control unit 30 includes a priority imaging data determiner 31 configured to determine the priority imaging data to be collected with priority, among the k-space data, and controls the measuring unit 10 in a manner that controls the signal acquisition order so that the measuring unit 10 collects the priority imaging data in advance. The control unit 30 further includes a status determiner 33 configured to determine the signal acquisition status in the measuring unit 10, and to allow the image generator 21 to perform image reconstruction using the priority imaging data, when the status determiner 33 determines that the priority imaging data has already been collected by the time when the measurement is aborted by the measuring unit 10.

Figure 2B:
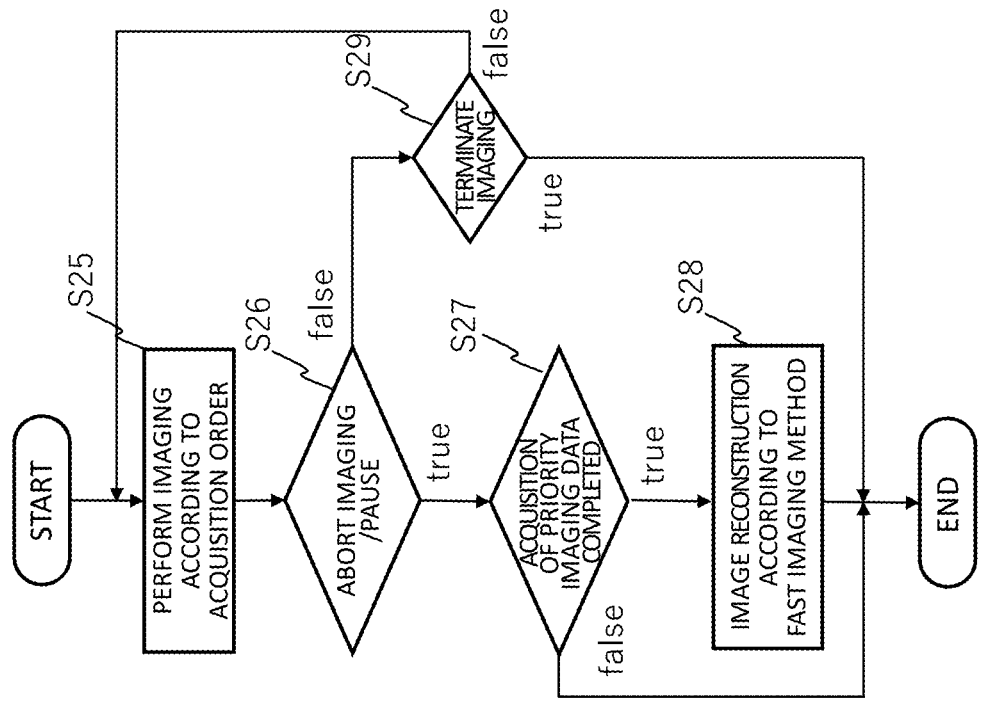
FIGS. 2A and 2B are flow diagrams showing the operation of the MRI apparatus.
Figure 2A:
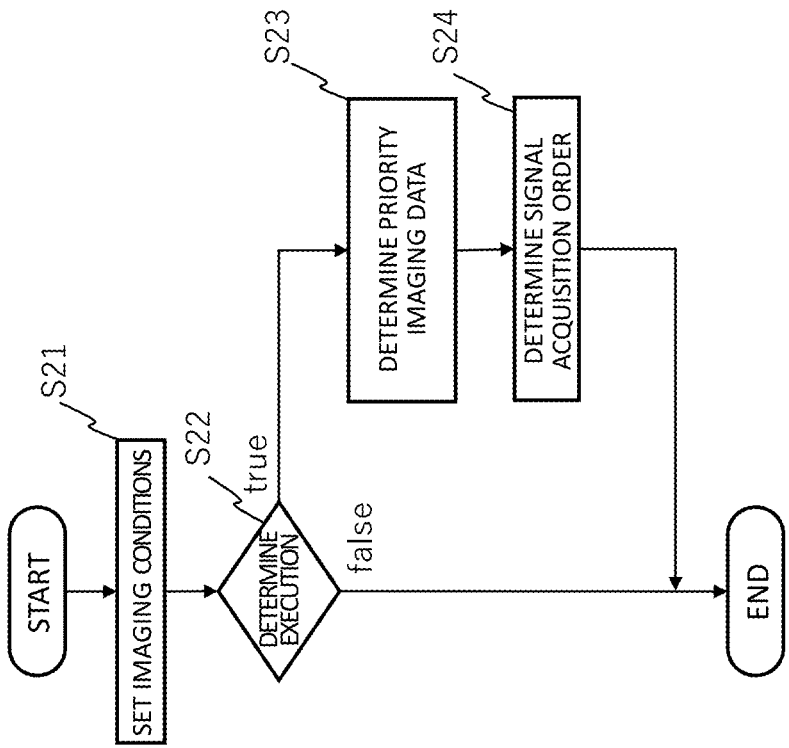

FIGS. 2A and 2B show the processing of the imaging control in the MRI apparatus. First, upon imaging, when the imaging conditions are set (S21), it is determined whether the function of collecting the priority imaging data in advance is selected (S22). If it is selected, the priority imaging data is determined (S23), and then the signal acquisition order is determined for the entire k-space including the priority imaging data (S24). The priority imaging data is less in the number of data than the k-space data determined by the imaging conditions, and also the priority imaging data is available for the image reconstruction according to a fast-imaging method. A configuration of the priority imaging data varies depending on the fast-imaging method. The imaging method included in the imaging conditions may decide which fast imaging method is to be selected, or any fast-imaging method implementable in the apparatus may be registered in advance.

Information related to the priority imaging data and the signal acquisition order, being determined in the above steps S23 and S24, is transferred to the sequencer, and the sequencer calculates the pulse sequence using this information, and starts imaging (S25). If the function is not selected in S22, imaging is started with initially set imaging conditions.

If the imaging is aborted in the ongoing imaging process (S26), it is determined whether the priority imaging data has been collected by that time (S27). If it has been collected, the image generator 21 uses the priority imaging data to perform a computation for the image reconstruction according to the fast-imaging method, and generates an image (S28). The image may be stored in a storage device as needed, or displayed on a display device. If collection of the priority imaging data is not completed at the point of aborted imaging, the imaging is terminated.

There will now be described a specific device configuration of the MRI apparatus including the measuring unit 10, the computing unit 20 (the image generator 21), and the control unit 30 as described above.

Figure 3:
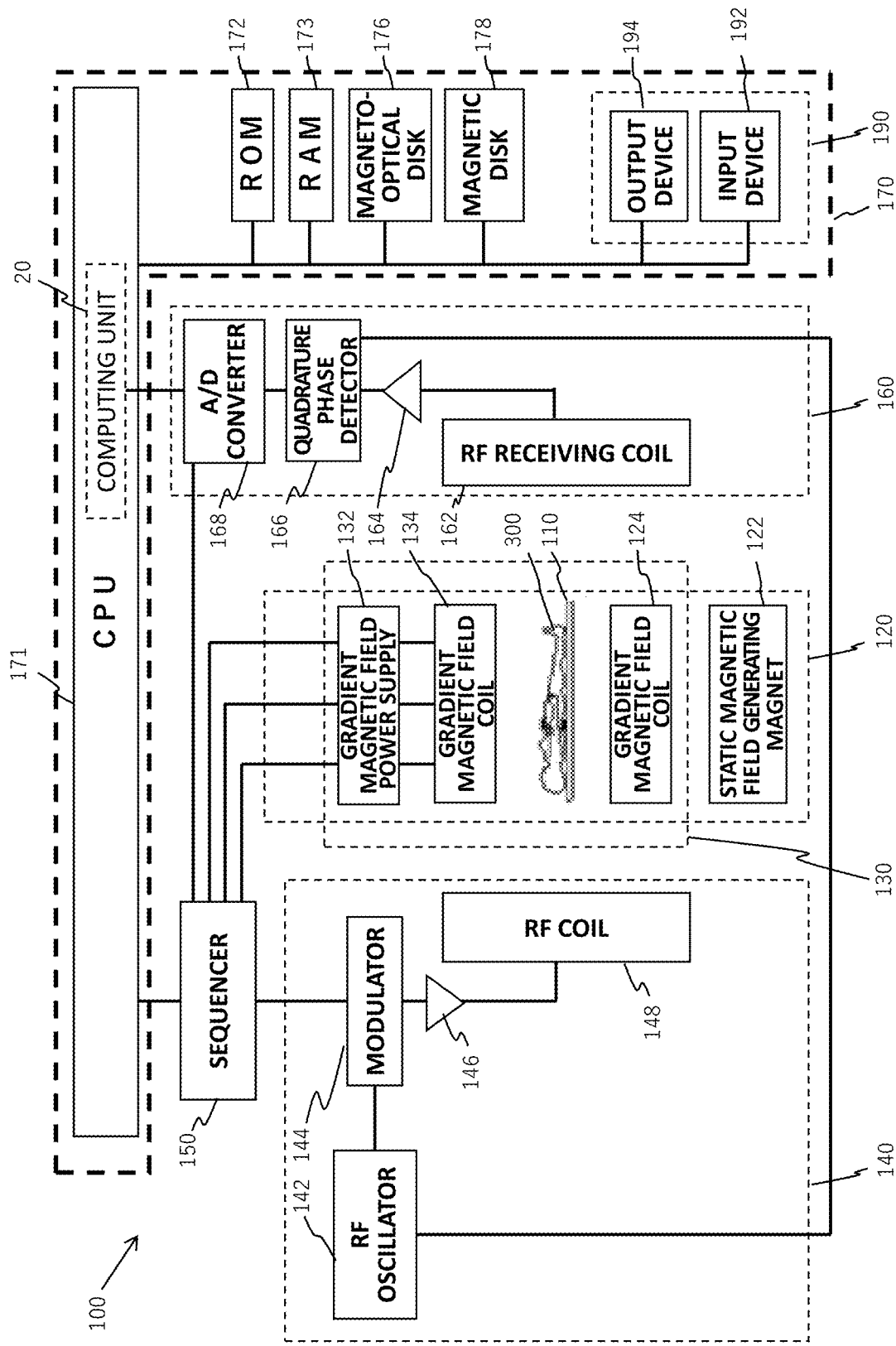
FIG. 3 is a diagram showing an overall configuration of the MRI apparatus.

FIG. 3 is a block diagram showing one embodiment of the MRI apparatus 100. The MRI apparatus 100 includes a static magnetic field generator 120 configured to generate a static magnetic field, a gradient magnetic field generator 130, an RF pulse transmitter 140, an RF signal receiver 160, a controller 170 having the functions of the computing unit 20 and the control unit 30, a sequencer 150, and a table unit 110 having a top plate for placing the subject 300 thereon. The static magnetic field generator 120, the gradient magnetic field generator 130, the RF pulse transmitter 140, the RF signal receiver 160, and the sequencer 150 correspond to the measuring unit 10 in FIG. 1.

The sequencer 150 controls, based on a control command from the controller 170, the operations of the gradient magnetic field generator 130, the RF pulse transmitter 140, and the RF signal receiver 160.

The static magnetic field generator 120 is provided with a static magnetic field generating magnet 122 for generating a homogeneous static magnetic field in a direction perpendicular to the body axis direction or a direction of the body axis of the subject 300 in the measurement space where the subject 300 is disposed, and a driving system (not illustrated) for driving the magnet. As a mode of magnetic field generation of the static magnetic field generator 120, there are a permanent magnet system, a normal conduction system, a superconducting system, and so on. The present invention is applicable to any of the systems. The subject 300 is placed on the top plate of the table unit 110, and is disposed in the measurement space.

The gradient magnetic field generator 130 has gradient magnetic field coil 134 wound in the triaxial direction of X-axis, Y-axis, and the Z-axis, for example, and a gradient magnetic field power supply 132 for supplying drive current for generating a gradient magnetic field to each of the coils in the triaxial direction. The gradient magnetic field power supply 132 supplies a drive current to the gradient magnetic field coil 134 wound in the triaxial direction, X-axis, Y-axis, and Z-axis described above in accordance with a control command from the sequencer 150. Thus the gradient magnetic field coil 134 generates gradient magnetic fields Gs, Gp, and Gf, respectively in the triaxial direction of the X-axis, Y-axis, and Z-axis, and these gradient magnetic fields are applied to the subject 300.

When the gradient magnetic field Gs is applied to the subject 300, a slice plane provided, which is an imaging cross section. Further, a phase-encoded gradient field Gp and a frequency-encoded gradient field Gf are applied in the remaining two directions, orthogonal to the slice plane and orthogonal to each other, to encode the position information into the NMR signal generated from the slice plane of the subject 300. Though not illustrated, a shim coil may be provided, for example, for compensate for the inhomogeneity of the static magnetic field.

The RF pulse transmitter 140 includes an RF oscillator 142, a modulator 144, an RF amplifier 146, and a transmission-side RF coil 148. In order to cause NMR phenomenon in the nuclear spin of the atoms constituting the biological tissue of the subject 300, the subject 300 is irradiated with an RF magnetic field pulse (hereinafter, referred to as RF pulse). That is, the RF oscillator 142 generates an RF pulse and outputs the RF pulse to the modulator 144 at a timing based on a control command from the sequencer 150. The modulator 144 amplitude-modulates the inputted RF pulse, and the amplitude-modulated RF pulse is amplified by the RF amplifier 146 and supplied to the RF coil 148 disposed in proximity to the subject 300. The RF coil 148 applies RF pulses based on the supplied RF pulses to the subject 300. The irradiation of the RF pulses causes NMR phenomenon in the nuclear spin of the atoms constituting the biological tissue of the subject 300, and the NMR signal is emitted as an echo signal.

The RF signal receiver 160 has a function of detecting the NMR signal being the echo signal emitted from the nuclear magnetic resonance phenomenon in the nucleus of the biological tissue of the subject 300, and the RF signal receiver comprises an RF receiving coil 162, an amplifier 164, a quadrature phase detector 166, and an A/D converter 168. The NMR signal is emitted from the subject 300, in response to the RF pulse applied from the RF coil 148 to the subject 300, and the emitted NMR signal is detected by the RF receiving coil 162, followed by amplification by the amplifier 164, then the quadrature phase detector 166 divides the amplified signal into orthogonal two systems of signals based on the timing according to a command from the sequencer 150, and each of the signals is converted into a digital amount by the A/D converter 168. The signals converted into the digital amount are sent to the image generator 21, and stored in the data space called k-space (storage area), and then the stored data becomes k-space data. It should be noted the RF receiving coil 162 includes a plurality of receiving coils, and each of the receiving coils receives the NMR signal being the echo signal.

The controller 170 includes a central processing unit (hereinafter, referred to as CPU) 171, an input-output device (UI device) 190 having an input device 192 and an output device 194, and a storage device such as a magneto-optical disk 176 and a magnetic disk 178, and the controller has a function as the computing unit 20 of FIG. 1, a function as the control unit 30 for performing overall control of the MRI apparatus 100, and functions of supporting user's information entry and imaging parameter setting. Here, among the functions of the computing unit 20, the functional unit that relates to image generation shall correspond to the image generator 21 in this example.

The output device 194 includes, in addition to the display device and a printer provided in an operation room, a display device provided on the gantry of the MRI apparatus 100. The input device 192 also includes, for example, a pointing device including a keyboard, a trackball, and a mouse, and a touch panel or a keyboard integrally provided to the output device 194. Conditions and necessary information for the examination are entered via the input device 192, and also manipulations for executing the examination and instructions for the processing are performed via the input device 192. On the display device in the output device 194, there are displayed, information for prompting entry of the conditions and information necessary for the examination as described above, or information for assisting to provide instructions for the manipulation and the processing, and information actually entered or the information representing the manipulation status. Furthermore, the image generator 21 displays an MRI image and others as a result of the processing.

The CPU 171 is accompanied with a read-only memory (hereinafter, referred to as ROM) 172 and a random-access memory (hereinafter, referred to as RAM) 173, and others. The ROM 172 stores programs that are executed by the CPU 171, for example, programs for performing image analysis processing and measurement over time, and parameters that remain unchanged for use in executing the programs. In addition, the RAM 173 stores data such as the measurement parameters and measured data obtained by previous measurement, and parameters for setting a region of interest. The CPU 171 reads the programs from the ROM 172, and executes the functions as the control unit 30 and the computing unit 20 described above.

The control unit 30 sets a pulse sequence used for imaging, based on the examination conditions including the imaging parameters entered via the input-output device 190 by the operator. The pulse sequence is a pulse train, for example, arranging RF pulses or gradient magnetic field pulses in time series along a certain rule being provided, and there are prepared various pulse sequences depending on the imaging method. This pulse sequence determines the order of the measurement data arrangement in k-space comprising the NMR signals (digital signals), that is, the order of NMR signal acquisition. The control unit 30 (the priority imaging data determiner 31 in FIG. 1) determines the measurement data to be acquired with priority (priority imaging data) in the k-space, when setting the pulse sequence.

The sequencer 150 activates the RF pulse transmitter 140, the gradient magnetic field generator 130, and the RF signal receiver 160, based on the pulse sequence being provided and the signal acquisition order being determined, and performs control for repeatedly applying RF pulses to the subject 300, causing NMR phenomenon in the nuclei of the atoms constituting the biological tissue of the subject 300, and also for detecting and converting generated NMR signals (echo signals) into digital signals.

The control unit 30 (the status determiner 33 in FIG. 1) further determines whether the image reconstruction process is performed utilizing the measurement data, or the measurement data is discarded, in response to the status of the measurement data collected so far, thereby controlling the operation of the image reconstruction by the image generator 21.

The computing unit 20 has functions of performing the Fourier transform and the correction factor calculation on the measurement data (k-space data) based on the NMR signals detected by the RF signal receiver 160, performing the image reconstruction of the image, and displaying thus reconstructed image on the output device. The image reconstruction performed by the image generator 21 comprises an image reconstruction operation based on a fast-imaging method including parallel imaging and iterative reconstruction such as and compressed sensing, and the image generator 21 performs the image reconstruction using a predetermined computing method, under the control of the control unit 30. The computation for the image reconstruction is incorporated, for example, in the ROM 172 in advance in the form of programs as described above.

In the example shown in FIG. 3, the controller 170 implements the function of the computing unit 20, but the computing unit 20 may be implemented by an independent processing unit that is different from the controller 170. The CPU 171 of the controller 170 comprehensively controls the MRI apparatus 100, also controls the sequencer 150, and further functions as the computing unit 20. However, it is also possible to consider independent units having the same respective functions operate independently. Any configuration is available for these independent units, and the present invention is applicable to any of the configurations.

The reconstructed image data and other similar data may be stored in a storage device such as the magneto-optical disk 176 and the magnetic disk 178. Then, such data is read out from the storage device, and displayed on the output device (display device) 194 in the form of a tomographic image, for example.

In view of the configuration of the MRI apparatus as described above, there will now be described the control of the measuring unit 10 and the image generator 21, performed by the control unit 30 in accordance with the specific imaging method. In particular, embodiments of the control for determining the priority imaging data and the control of the signal acquisition order will be described. In the following embodiments, the basic device configuration and the processing of the control are the same as those as shown in FIGS. 1, 2 and 3, and hereinafter, these drawings will be referred to as appropriate.

First Embodiment

In the present embodiment, parallel imaging is used to output an image from the imaging data at the time when imaging is aborted. The parallel imaging is a fast-imaging method for under-sampling the k-space data, and a ratio of under-sampling varies according to a reduction factor (R factor) of the parallel imaging. In the present embodiment, the imaging data required in accordance with the R factor of the parallel imaging, is set as the priority imaging data, and the imaging is performed in the imaging order that the priority imaging data is measured first, followed by measurement of the remaining k-space data. In this situation, if the imaging is not aborted, normal image reconstruction is performed using all the k-space data acquired. Only the change in the imaging order may not change the imaging time, nor deteriorate the image quality. In the case where the imaging is aborted, if all the priority imaging data has already been acquired, image reconstruction is performed by the parallel imaging utilizing the priority imaging data, and an image is generated. Data other than the priority imaging data is discarded without being used, because the data is assumed as including, for example, a motion of the subject, immediately before the imaging is aborted.

Figure 4:
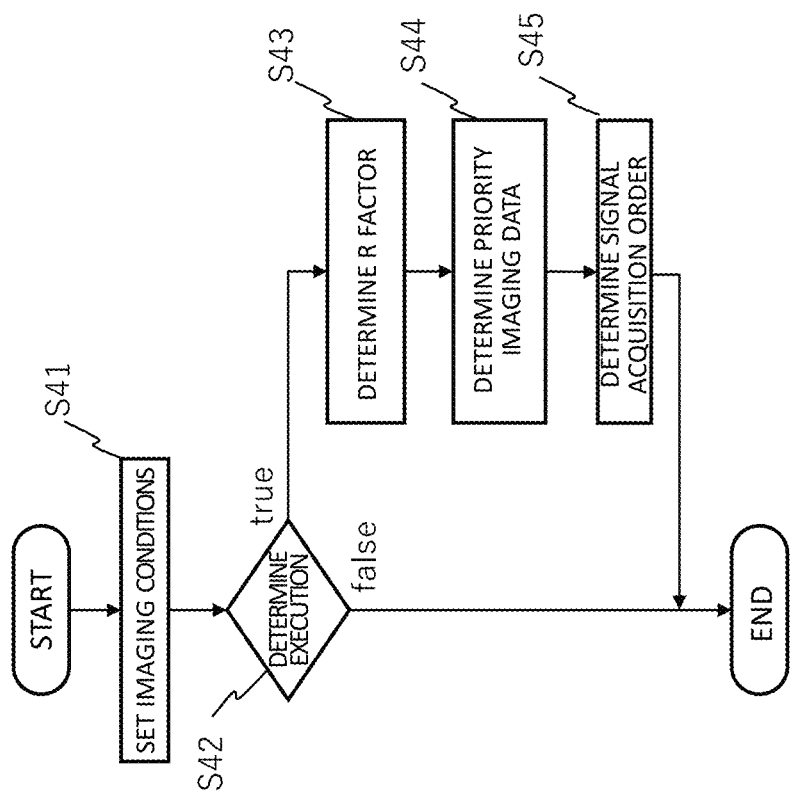
FIG. 4 is a flowchart showing determination of a signal acquisition order in the MRI apparatus according to a first embodiment.

With reference to FIGS. 4 to 7, a specific operation example of the MRI apparatus according to the present embodiment will be described. FIG. 4 is a flowchart relating to the control during the imaging. First, the control unit 30 sets the pulse sequence based on the imaging conditions entered via the input device 192 (S41), and determines the feasibility of the function for outputting an image from the data at the aborted point (S42). The function for outputting the image from the data at the aborted point is determined as feasible when the followings are satisfied: That is, there is selected the function for generating an image from the data measured by the time when the imaging is aborted, and the image generator 20 is provided with a computing function for performing the parallel imaging, that is, it is provided with programs for the computation.

In S42, when it is determined as feasible, the R factor of the parallel imaging (the under-sampling rate of k-space data) is determined to perform the image reconstruction from the data at the aborted point (S43). When the R factor is great, the amount of data for outputting an image is reduced, and this can reduce data to be wasted, but at the same time, the SNR may be lowered and artifacts may occur due to the great R factor. The R factor may be determined by a user depending on conditions of the subject, or may be determined as a predetermined value. Alternatively, the control unit 30 may decide the R factor according to the device condition, for example, the number of the receiving coils and the arrangement thereof.

Figure 5:
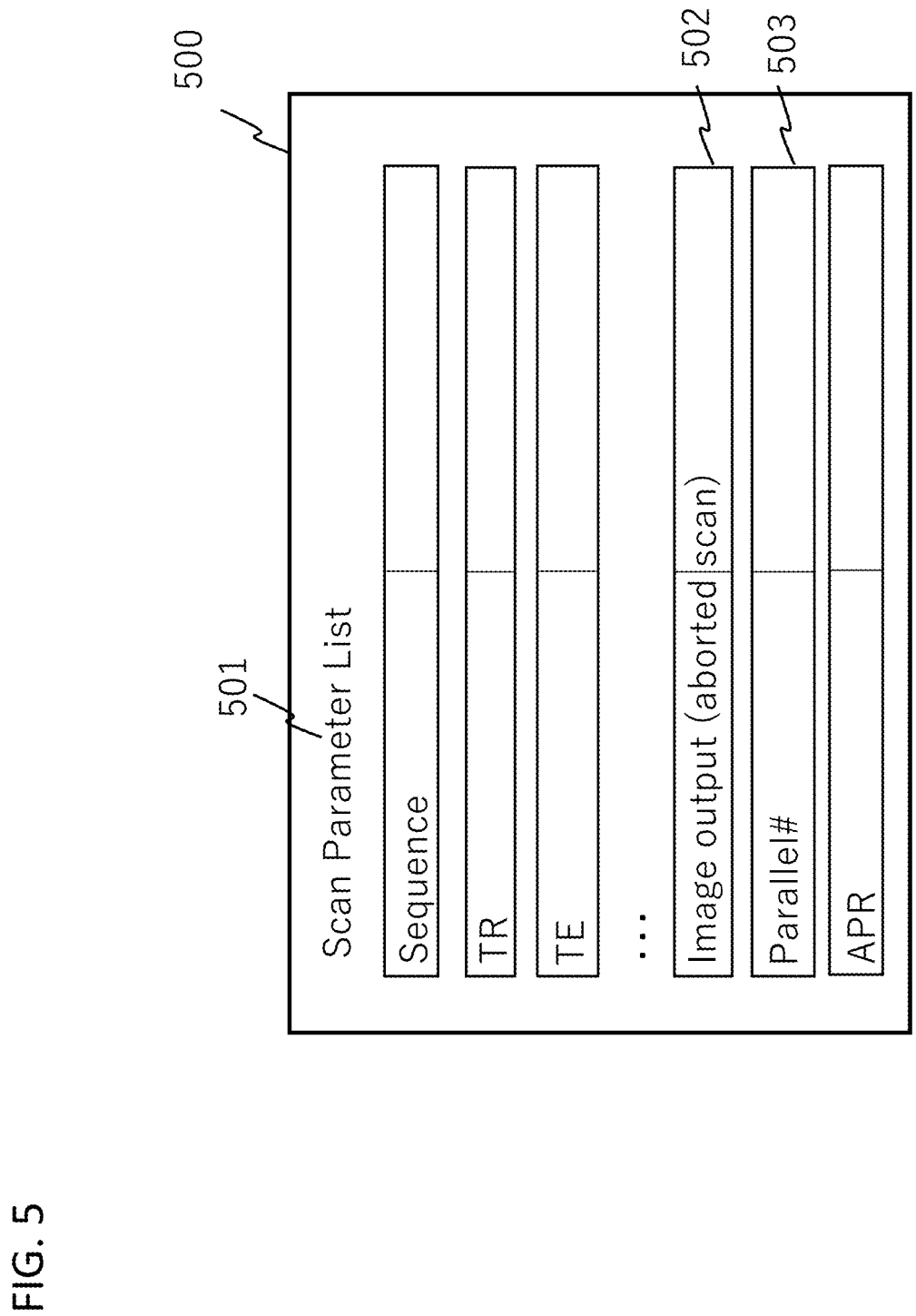
FIG. 5 illustrates an example of a GUI for setting imaging conditions displayed on a display device.

FIG. 5 shows an example of the GUI screen 500 in the case where the user performs determination on the execution in S42 or the setting of an R factor of the parallel imaging in S43. In this example, in addition to setting blocks for "Scan Parameter List" 501, for selecting the pulse sequence of the imaging, together with setting the imaging parameters TR (repetition time), TE (echo time), and others, there are provided entry blocks such as "Image Output (aborted scan)" 502 and "Parallel #" 503 are provided. Selecting the "Image Output (aborted scan)" 502 causes a selection of the function for performing the image reconstruction from the data at the aborted point, and the R factor is inputted in the entry block of "Parallel #" 503.

When the R factor is determined in S43, the priority imaging data determiner 31 determines the priority imaging data based on the R factor thus entered (S44), and also determines the acquisition order of the signals in the k-space (S45).

Figure 6:
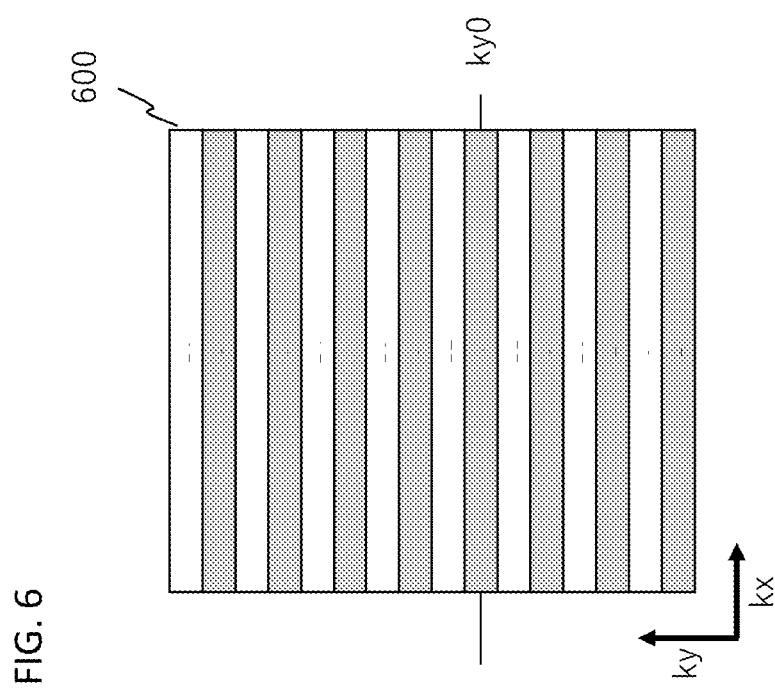
FIG. 6 illustrates priority imaging data according to the first embodiment.

FIG. 6 illustrates an example of the signal acquisition order when the R factor is set to two (double-speed). In this example, there is briefly shown the k-space data 600 with the matrix size of 16 in the ky direction. As illustrated, every other measurement point is assumed as the priority measurement point (gray in color), out of 16 measurement points along the ky direction. The signal acquisition order is determined in a manner that acquires the measurement points to be prioritized first, followed by acquiring the remaining measurement points, and the phase encoding is performed so that the signals are stored in the k-space in thus determined order of the signal acquisition. In FIG. 6, the numbers in the k-space represent the order in which the measurement is performed, and the priority imaging data is captured in the order from the first to the eighth. In this example, both the priority imaging data and the non-priority imaging data are acquired sequentially in the order from one edge to the other in the ky direction of the k-space. However, the imaging can be performed in any order within each of the priority imaging data and the non-priority imaging data.

Instead of fixing the R-factor to two (double-speed), it is also possible to combine a plurality of R factor, and the priority imaging data may be provided in multiple stages. For example, the priority imaging data 1 to 8 in the k-space data as shown in FIG. 6 may be divided into two groups; the first priority imaging data [1, 3, 5, 7] and the second priority imaging data [2, 4, 6, 8], and the signal acquisition order may be set to acquire one group preceding to the other group. This enables acquisition of the priority imaging data at R factor of four. Also in this case, the signal acquisition order within one group of the priority imaging data is not particularly limited. By way of example, imaging may be performed in the acquisition order of 1→3→5→7, then in the order of 2→4→6→8.

Subsequently, with reference to FIG. 7, there will be described the processing of control after the imaging is started.

After the imaging is started (S71), if the imaging is neither aborted nor paused by the user (S81) and the imaging is completed normally (S73), normal image reconstruction is performed to output an image (S74). When the imaging is aborted (S72), the status determiner 33 determines whether all the priority imaging data has already been acquired (S75). In the example of FIG. 6 in which double speed is set as the R factor, if the data items equal to or more than eight and less than 16 have been acquired, image reconstruction is performed by the parallel imaging, using the acquired first to the eighth priority imaging data, and an image is outputted in step S76. If all of the priority imaging data has not been acquired, the imaging data is discarded and the imaging is terminated (S73).

In the case where a plurality of R factor is combined and a plurality of priority imaging data items with different priorities are provided, when the imaging is aborted, for example, even though not all of the priority imaging data of double-speed has not been acquired, if all the priority imaging data items of R factor of 4 have been acquired, the image generator 20 performs image reconstruction by the parallel imaging with the R factor of 4 (S72 to S76). This enables reduction of discarded and wasted data. The image generated by the image generator 20 is outputted to the output device 194.

Aborted imaging may include termination due to reasons such as poor physical condition or drastic movement of the subject, as well as reasons in which the imaging is paused at the user's discretion due to a call for operator intervention (alert signal) from the examinee or reasons on the user side. In those cases as well, the user's instruction to pause is accepted via the input device (S81), and it is determined whether the image reconstruction can be performed as in the case of aborted imaging (S82). When all the priority imaging data has been obtained, the image reconstruction is performed (S83).

In the case of pausing, the image generated by the image generator 20 may be temporarily displayed as a preview image (S84). The user checks the preview image at the time of pausing due to any reason such as the alert signal from the examinee, allowing the user to determine whether re-imaging is possible, and this enhances the examination efficiency. After the pausing, if the imaging is not resumed (S84), the imaging is terminated (S73).

Figure 8:
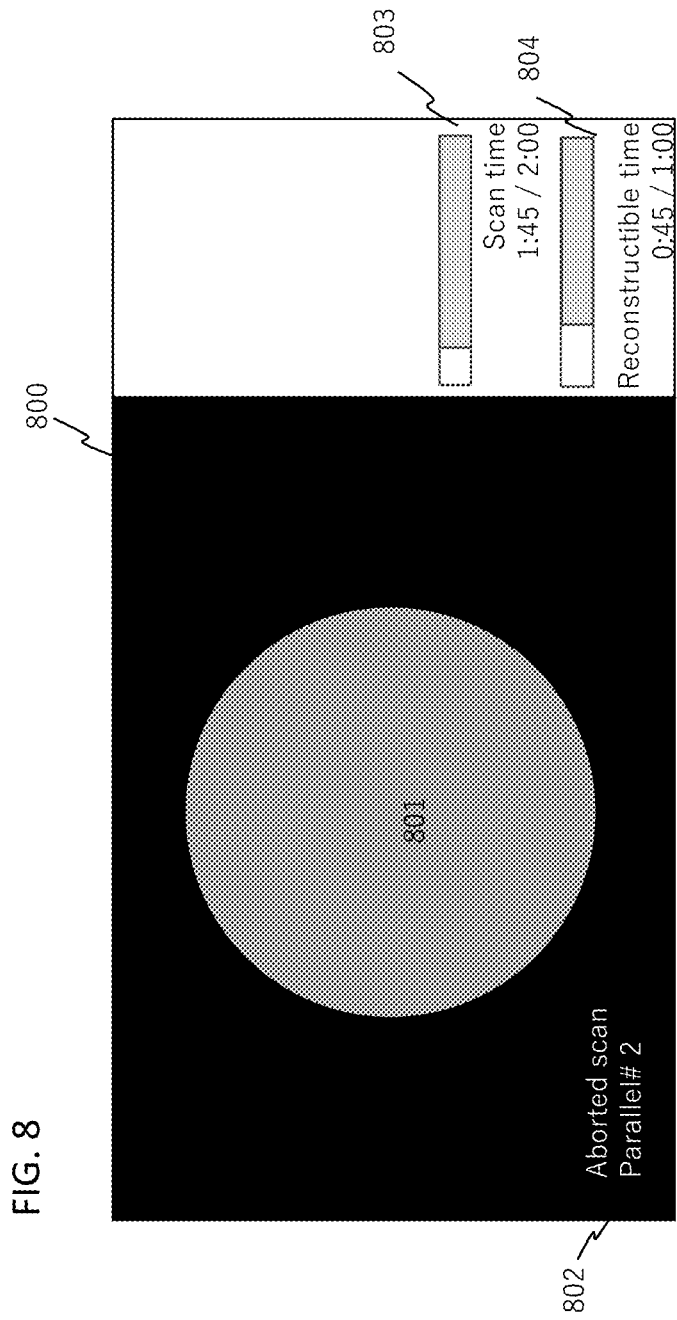
FIG. 8 illustrates an example of a signal acquisition status displayed on the display device.

FIG. 8 shows a display example 800 of the image that the image generator 20 has generated by using the data at the aborted point, after the imaging is aborted or paused in the present embodiment. In this example, information items indicating that the image was outputted at the time when the imaging was aborted, and the R factor of the parallel imaging used for the image reconstruction, are provided as the image information attached to the image data, and this attached information ("Aborted Scan Parallel #") 802 is displayed simultaneously with the captured image 801. With the information thus displayed, it is presented to the user that the image was captured at the time when the imaging was aborted, allowing the user to distinguish the image from other images, even mixed with the other captured images. In addition, displaying the information such as the R factor of the parallel imaging used for the image reconstruction, allows the user to be notified how the image has been reconstructed, and the user can determine whether or not re-imaging is required in addition to the outputted image.

Further, as shown in FIG. 8, there may be displayed the imaging time with down-counting, and the progress bar 803, the reconstructible time with down-counting, and the progress bar 804. For example, if the remaining time of the progress bar 803 is a few seconds, the imaging can be aborted after waiting that time, and the data can be utilized without being wasted in determining the imaging should be aborted or not. In the illustrated example, the imaging time (scan time) is shown in the form of the progress bar, but various forms may be available as a method for indicating the progress of the imaging, such as a percentage (%) display where the total imaging time is set to 100.

According to the present embodiment, the priority imaging data is determined in accordance with an R factor of the parallel imaging, and the measurement points of the priority imaging data are measured with priority, whereby the waste of the imaging data can be reduced as much as possible, even when the imaging is aborted or paused. In addition, different values of the R factor can be combined in a plurality of stages, and a priority in data acquisition is given to the data that is reconstructible at a greater R factor, thereby further reducing the number of data that has to be discarded.

Modification of First Embodiment

In the first embodiment, when the imaging is aborted, the parallel imaging reconstruction is performed where two-dimensional data in the k-space is under-sampled (decimated). In the case of 3D imaging, it is also possible to determine the priority imaging data so that the two-dimensional parallel imaging reconstruction is performed in the ky and kz directions at the time when the imaging is aborted. There will now be described a method for determining the priority imaging data in the case as described above.

In the two-dimensional parallel imaging, the priority imaging data is obtained according to the R factor of the parallel imaging for each axis. The R factor of the parallel imaging is determined for each of the two-dimensional directions (the phase direction and the slice direction). The R factor may be decided as a value predetermined in the system, or a user who performs the imaging may set the value via the GUI, as in the first embodiment.

In determining the priority imaging data, first, data items are obtained by under-sampling the data area in the k-space at the R factor on each axis, and the measurement point as an intersection of the data items is set as the first priority imaging data having the highest priority. Then, the measurement point enabling one-dimensional parallel imaging on each axis is set as the priority imaging data. Among the priority imaging data of both axes (excluding the first priority imaging data), any axis may be given a priority, and it may be determined according to the number of measurement points on each axis. Specifically, the measurement points on the axis enabling the one-dimensional parallel imaging, the number of which is smaller, are set as the second priority imaging data to be acquired subsequent to the first priority imaging data, and the measurement points on the remaining axis, enabling the parallel imaging, is set as the third priority imaging data. The signal acquisition order of the measurement points in each priority imaging data and the measurement points in the other area may be in any order, such as the order from one edge of k-space toward the other edge, and the order from the k-space center toward the edge.

If the first priority imaging data has already been obtained by the time when the imaging is aborted, the image reconstruction is performed at the R factor of the parallel imaging, which is set in each of the ky direction and the kz direction. If both the first and second priority imaging data have been acquired, the image reconstruction is performed by the one-dimensional parallel imaging. In this situation, when all the data in the ky direction has been acquired, the image reconstruction is performed at the R factor of the parallel imaging of the kz direction, and when all the data in the kz direction has been acquired, the image reconstruction is performed at the R factor of the parallel imaging in the ky direction. When the first, second, and third priority imaging data have been acquired, one-dimensional parallel imaging in the ky direction and in the kz direction can be performed, but it is performed on the axis having a smaller R factor of the parallel imaging. It is because SNR reduction and artifacts can be prevented more when the R factor is smaller. When all the imaging data has been obtained without aborting the imaging, normal image reconstruction is performed to output an image.

A basic concept of the present modification has been described so far. Hereinafter, with reference to FIGS. 9 to 11, there will be described a specific example for determining the priority imaging data and the order of imaging, and a specific example of the imaging and image reconstruction control based on the determination.

Figure 9:
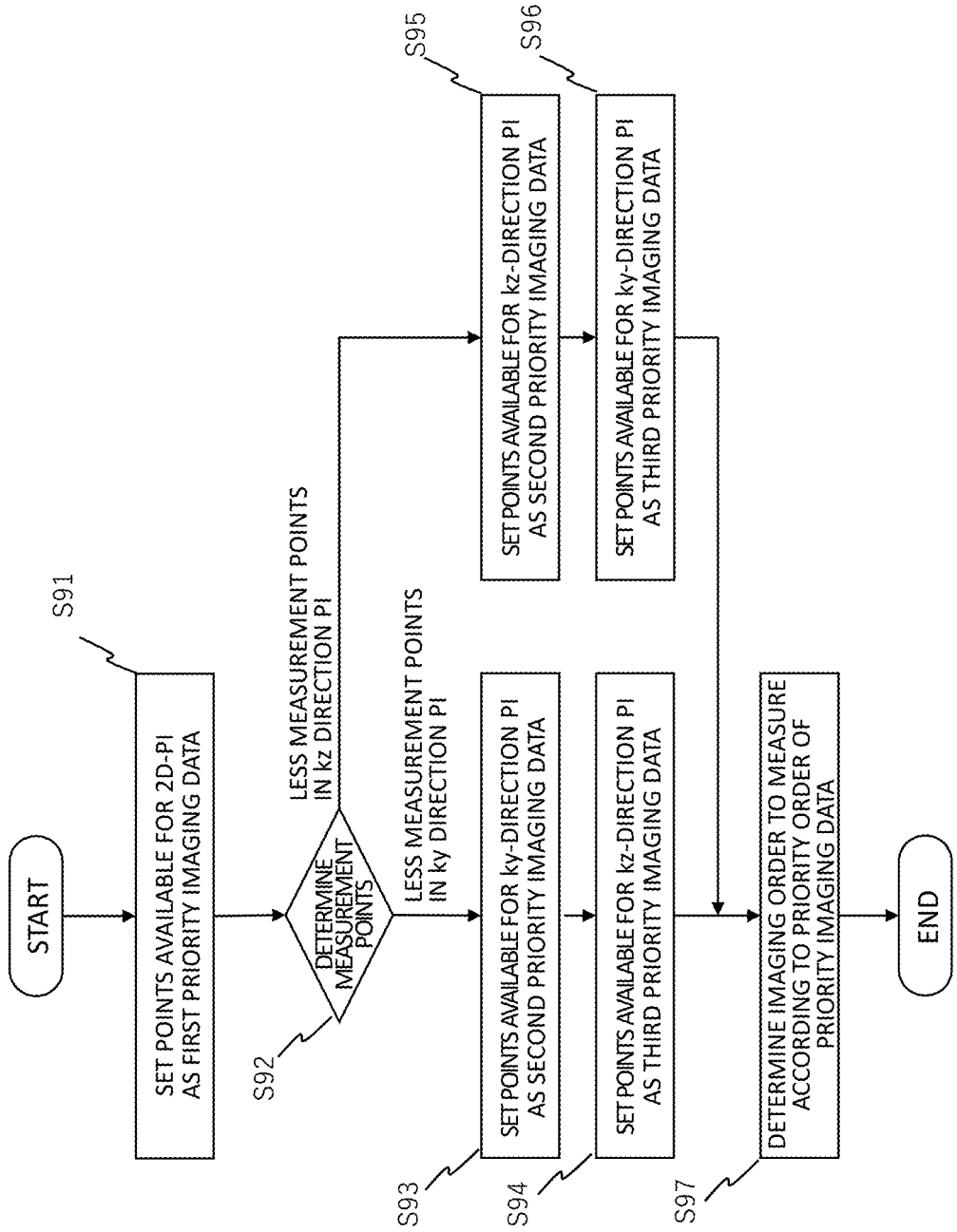
FIG. 9 is a flowchart showing the determination of the signal acquisition order in the MRI apparatus according to a modification of the first embodiment.
Figure 10:
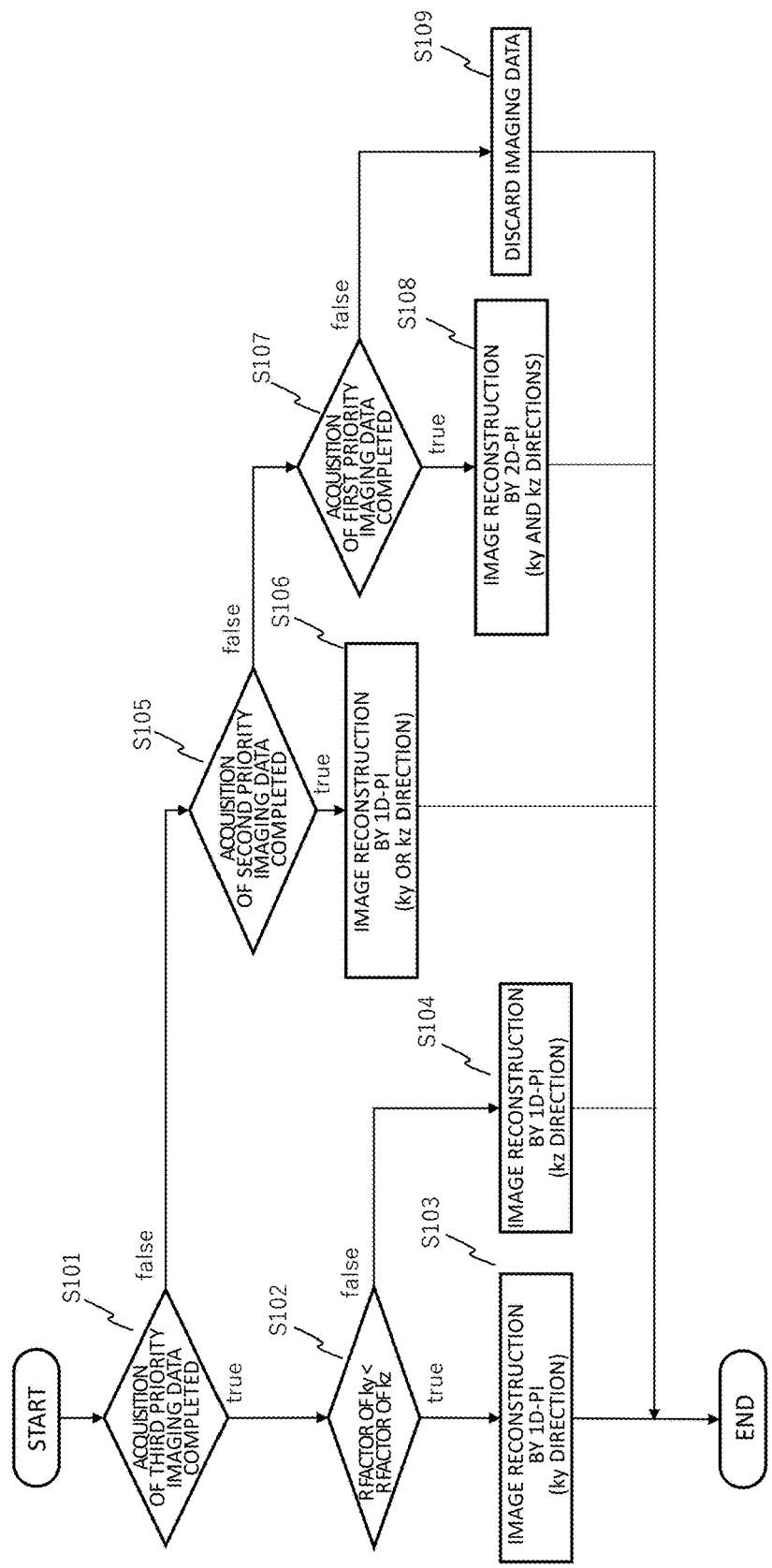
FIG. 10 is a flowchart showing the control at the time of imaging according to the modification of the first embodiment.
Figure 11:
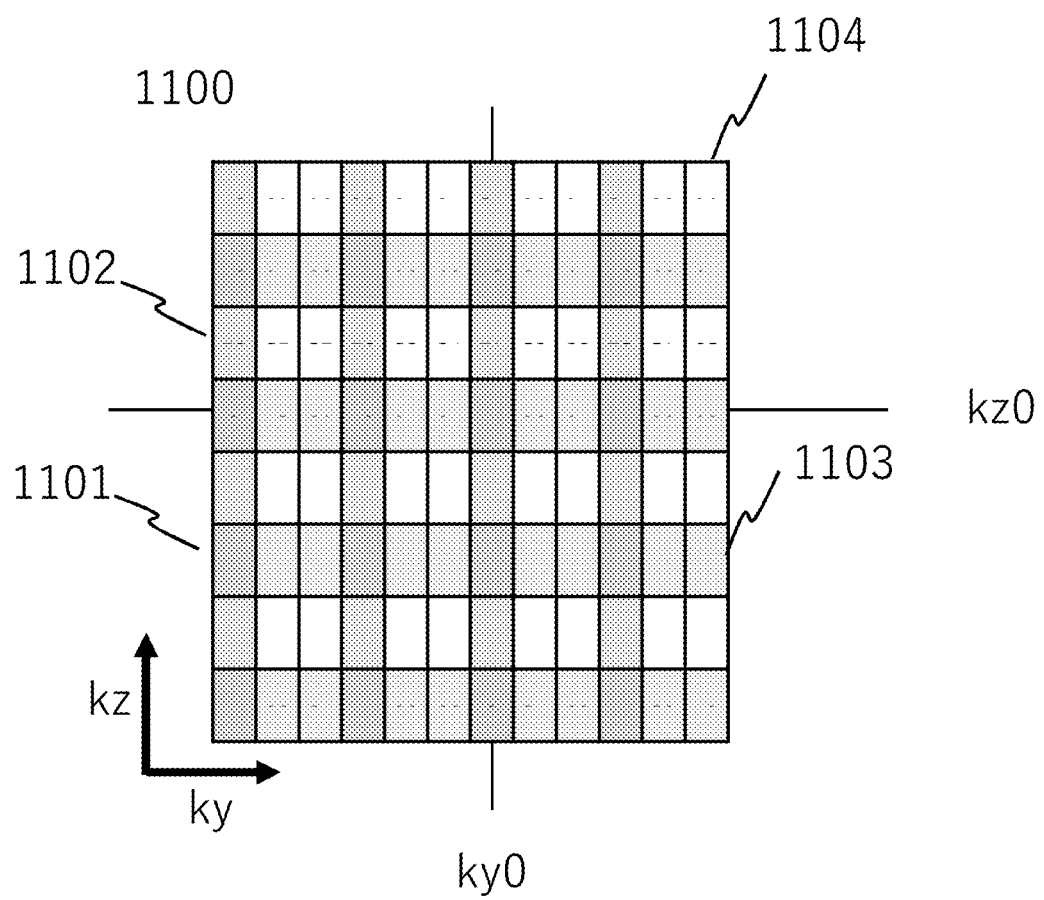
FIG. 11 illustrates the priority imaging data and the acquisition order according to the modification of the first embodiment.

FIG. 9 is a flowchart showing the determination of the signal acquisition order of the two-dimensional parallel imaging (PI), and FIG. 10 is a flowchart showing the imaging and image reconstruction. FIG. 11 illustrates an example of the priority imaging data in k-space (ky-kz section) setting triple-speed in the ky direction and double-speed in the kz direction. In FIG. 11, the measurement points shown in gray indicate the points that are reconfigurable by the parallel imaging (hereinafter, referred to as PI measurement points) at the speed multiplication factor of each axis. The measurement points are provided at every third point in the ky direction, and at every second point in the kz direction. The numbers respectively assigned to the measurement points indicate the order of acquisition.

As shown in FIG. 9, when the speed multiplication factor is determined, the priority imaging data determiner 31 first determines the measurement point of the first priority imaging data (referred to as priority measurement point) (S91). In the k-space 1100 as shown in FIG. 11, the first priority measurement points correspond to the measurement points 1101 that are intersections of the PI measurement points in the ky direction and the PI measurement points in the kz direction. In the example shown, they correspond to the 1st to the 16th measurement points.

Subsequently, the measurement points of the second priority imaging data (second priority measurement points) are determined (S92 to S96). The second priority measurement points are set to the PI measurement points 1102 on the axis where the number of PI measurement points available for the one-dimensional parallel imaging is smaller. The measurement points on the axis with the smaller number of the PI measurement points, which are remaining after acquiring the first priority imaging data, are determined as the second priority measurement points. This allows prompt execution of the one-dimensional imaging. In the example of FIG. 11, after the first priority imaging data is acquired, in order to perform the parallel imaging in only one-dimensional direction, the necessary number of data points is 16 points in the ky direction, whereas 32 points in the kz direction. Therefore, the PI measurement points in the ky direction are determined as the second priority measurement points, thereby enabling the one-dimensional parallel imaging to be performed more promptly. In this example here, the PI measurement points from the 17th to the 32nd in the ky direction (except the measurement points of the first priority imaging data) are determined as the second priority measurement points.

Then, the PI measurement points in the kz direction, i.e. the measurement points 1103, from the 33rd to 64th, excluding the measurement points of the first priority imaging data, are determined as the third priority imaging data. Data of the measurement points other than the PI measurement points shall be acquired in the signal acquisition order starting from the 65th point.

In the example as shown in FIG. 11, the data items are acquired in the sequential order within the priority imaging data, but the data items within each of the priority imaging data may be acquired in any order. In addition, the measurement points of the parallel imaging are determined with reference to the data at the edge, but the reference is not necessarily the data at the edge.

Next, there will be described the operation of the measuring unit 10 and the image generator 21 at the time of imaging. First, the measuring unit 10 starts imaging according to the signal acquisition order that is determined in S92 to S96 in FIG. 9. First, echo signals are collected by encoding that combines the encoding step at every third point in the ky direction, with the encoding step at every second point in the kz direction as shown in FIG. 11, and the first priority imaging data items (the first to the 16th priority measurement points) are collected. Then, slice encoding in the remaining kz direction is performed, along with performing the same phase encoding as the first priority measurement points, and the 17th to the 32th priority imaging data items (the second priority imaging data) are collected.

After collecting the second priority imaging data, encoding in the ky direction is performed along with performing the slice encoding in the kz direction that is the same as the first priority measurement points. Then, the PI measurement points in the kz direction other than the first priority measurement points, i.e., the data items of the 33rd to the 64th measurement points (third priority imaging data) are collected. Finally, the remaining measurement points are subjected to imaging. In this example, the data items from the 65th to 96th are acquired.

Next, with reference to the flowchart in FIG. 10, there will be described the operation of the status determiner 33 and the image generator 21, relating to the image reconstruction using the two-dimensional parallel imaging, at the time when the imaging is aborted.

When the imaging is aborted, the status determiner 33 determines whether or not all the priority imaging data up to the third priority imaging data is acquired (S101). If all the priority imaging data has been obtained, one-dimensional parallel imaging is enabled for each of the directions of the ky and kz, and thus the R factor of the parallel imaging for each of the ky and kz axes is determined (S102). Then, the image reconstruction using the one-dimensional parallel imaging is performed in the direction where the R factor is smaller (S103, S104). As thus described, the parallel imaging is performed on the axis with the R factor being smaller. In this way, it is possible to output an image with preventing SNR reduction and generation of artifacts.

If it is determined the third priority imaging data has not been acquired in S101, it is then determined whether the imaging data up to the second priority imaging data has been obtained (S105). If the second priority imaging data has been acquired, the image reconstruction is performed by the one-dimensional parallel imaging on the axis available for one-dimensional parallel imaging, i.e., on the ky axis, in this example (S106). If it is determined that the second priority imaging data has not been acquired in S106, it is then determined whether the imaging data up to the first priority imaging data has been obtained (S107). If the first priority imaging data has been acquired, the image reconstruction is performed by the two-dimensional parallel imaging in the ky and kz directions (S108). If the acquired data does not satisfy the first priority imaging data, the imaging data is discarded (S109).

According to the present modification, in the case of 3D imaging, parallel-imaging reconfigurable measurement points in each axial direction of the k-space, and two-dimensional parallel-imaging reconfigurable measurement points, are respectively set as the priority imaging data, and thus when the imaging is aborted, the acquired imaging data can be used to generate an image, and this increases the chance of imaging without waste. In particular, the order is determined in a manner to acquire in advance the priority imaging data with fewer data points, among a plurality of priority imaging data items, it is possible to further increase an effect in reducing wasteful data.

Second Embodiment

In the first embodiment and the modification thereof as described above, the R factor of the parallel imaging is determined based on the imaging method having no constraint on the measurement order in k-space, and the priority imaging data is determined on the basis of the R factor. The present embodiment relates to the imaging method with constraint on the order of measuring in the k-space, and under this constraint, the data reconfigurable by the fast-imaging method such as the parallel imaging is determined as priority imaging data.

The imaging methods with constraint on the measurement order in k-space include the followings. For example, in the imaging employing the pulse sequence for collecting a plurality of echo signals with different echo times after a single excitation, the arrangement of the plurality of echo signals in the k-space is controlled in accordance with the characteristics required for an image. FSE (Fast Spin Echo) method which is one of such imaging methods and, hereinafter, the present embodiment will be described with an example of FSE.

Figure 12:
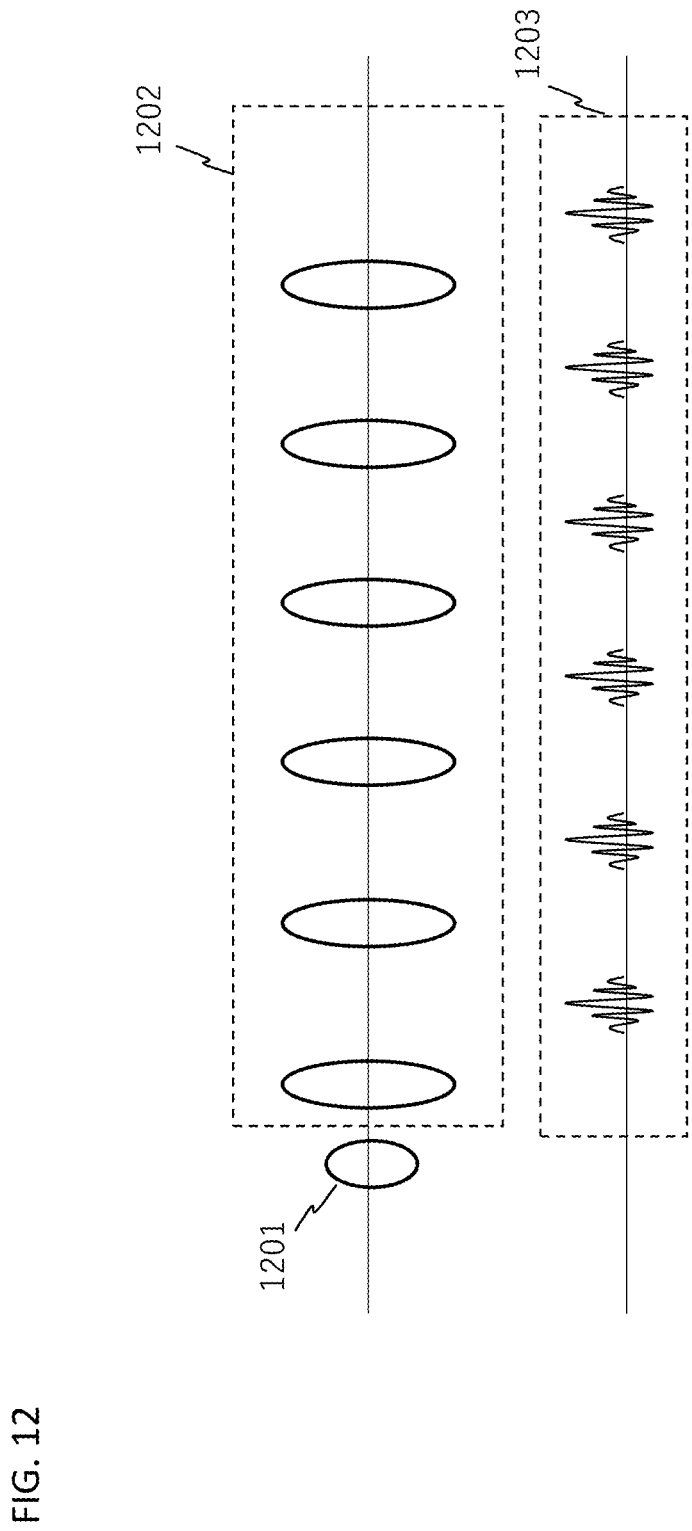
FIG. 12 illustrates an example of a pulse sequence (FSE) according to a second embodiment.
Figure 13:
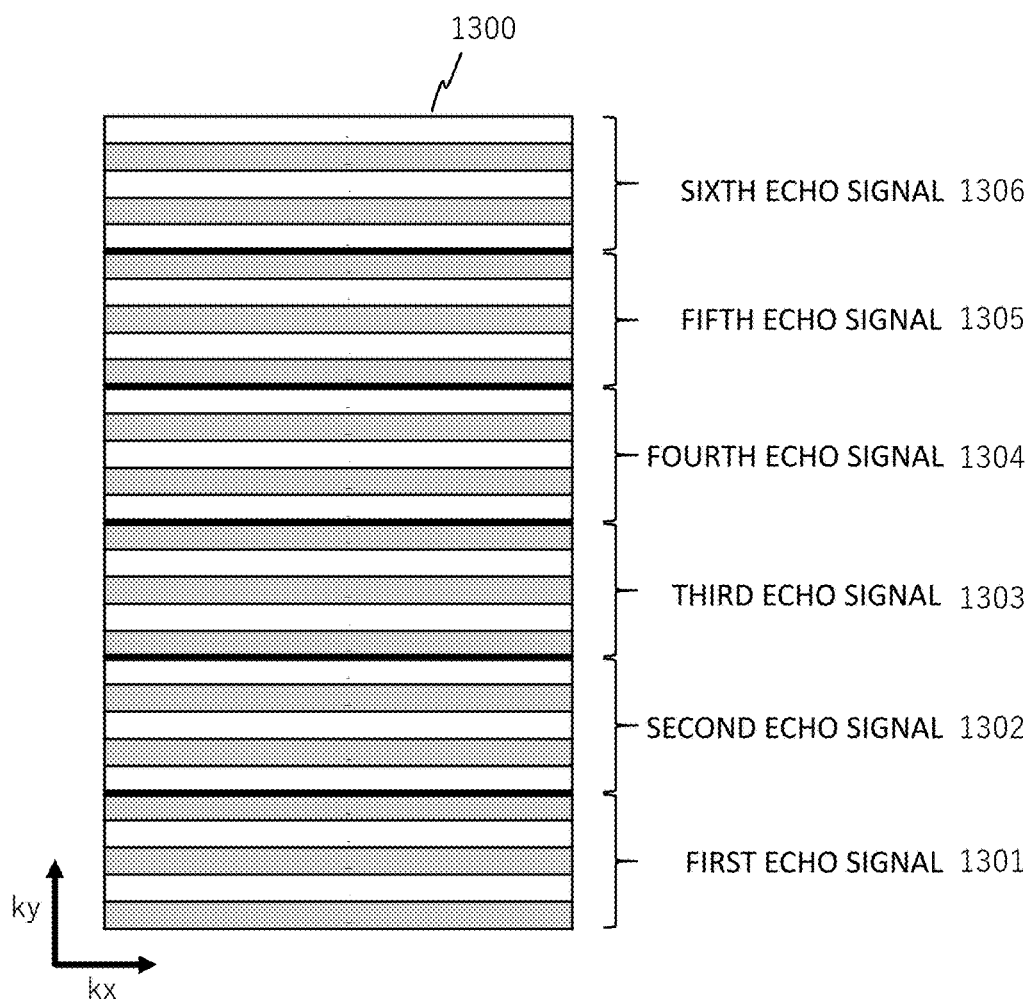
FIG. 13 illustrates an example of the priority imaging data and the acquisition order according to the second embodiment.

As shown in FIG. 12, an FSE sequence forms an echo train of multiple refocusing RF pulses 1202 in response to a single excitation RF pulse 1201 to acquire multiple echo signals 1203 with different TEs. Assuming that the number of imaging points is 30 and the number of echo train is 6, phase encoding is performed so that the measurement points obtained by dividing the k-space into six are respectively filled with the echo signals 1203. Consequently, the echo signals at respective TEs form the k-space data 1300 as shown in FIG. 13. In FIG. 13, the six regions delimited by the bold lines indicate the regions where the first to sixth echo signals are arranged, respectively. In this example, echoes from the first to the sixth are arranged from one edge of the k-space toward the other edge.

In this way, according to the FSE sequence, a plurality of echo signals simultaneously acquired with respect to the ky direction are arranged in a manner dispersed in the k-space. Thus, the signal acquisition order is determined so that the priority imaging data can be acquired for each echo of TE.

When the parallel imaging speed is doubled (R factor is 2), the priority measurement points are determined at every second point in the same manner as in the first embodiment (the measurement points shown in gray in FIG. 13). In the FSE sequence, however, echo signals corresponding to the number of echo train are acquired simultaneously, and thus the order of the imaging points is determined on an echo-by-echo basis. For example, in the first echo signal 1301, there are three priority measurement points, and thus the order is determined to perform imaging in advance up to the third priority measurement point. Since the number of the priority measurement points is two in the second echo signal 1302, the order is determined to perform imaging in advance up to the second priority measurement point. The signal acquisition order is determined in the similar manner, so as to acquire the priority measurement points in advance for each echo signal, and thereafter, the remaining measurement points are acquired. Then, phase encoding is performed so that the echo signals are stored in the k-space in thus determined order. In this example, the signal acquisition order is determined sequentially from the edge. However, the order of imaging may be changed within the priority imaging data and within the non-priority imaging data. Furthermore, it is also possible to change the order on an echo-by-echo basis.

Figure 7:
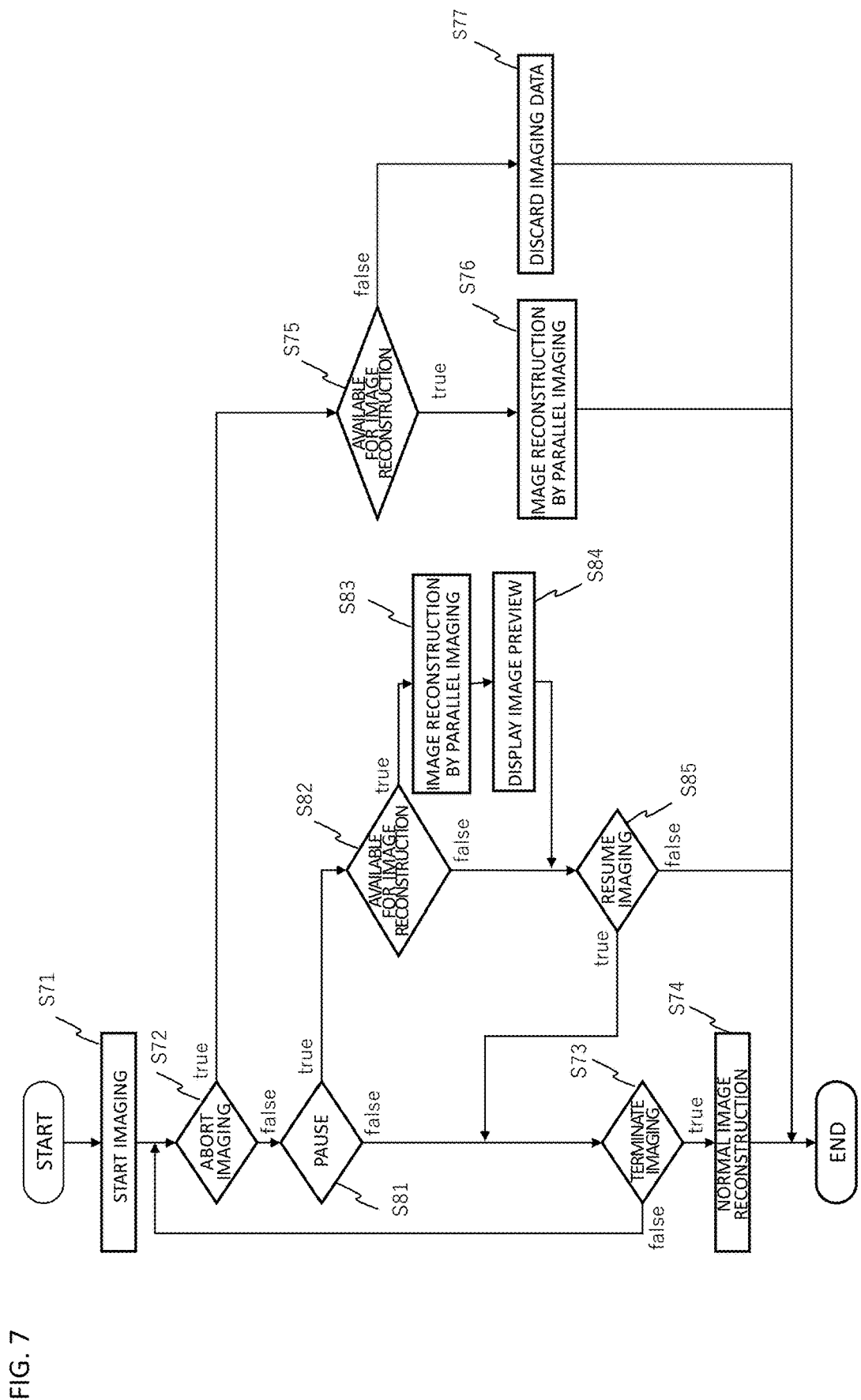
FIG. 7 is a flowchart showing a control at the time of imaging according to the first embodiment.

The processing relating to the image reconstruction is the same as the processing of the first embodiment as shown in FIG. 7, and redundant descriptions will not be given. Further, in the case of 3D FSE sequence, similarly to the modification of the first embodiment using the two-dimensional parallel imaging, a plurality of priority imaging data is determined. Image reconstruction according to parallel imaging being available is performed depending on how much of the plurality of priority imaging data has been acquired by the time when the imaging is aborted.

According to the present embodiment, even in the imaging method with a constraint on the k-space arrangement, the priority imaging data can be determined along the constraint. Accordingly, similarly to the first embodiment and its modification, it is possible to maximize the utilization of the acquired data for image generation, thereby reducing the data to be discarded when the imaging is aborted.

Modification of Second Embodiment

In the second embodiment, there has been described the FSE as an example of the imaging method with constraint on the order of acquiring the k-space data. There is also a technique of adjusting the acquisition order so as to reduce the influence of body motion (for example, the present applicant's application No. 2019-031754, hereinafter referred to as Patent Document 2). In this modification, the present invention is applied to the technique for compensating for body motion.

Figure 14A:
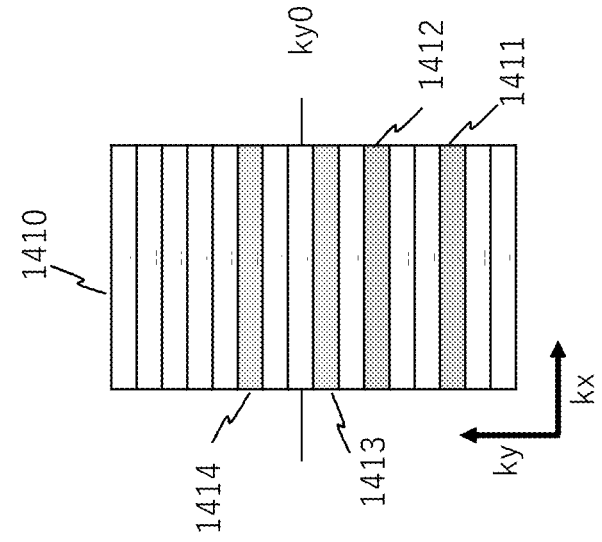
FIGS. 14A and 14B illustrate the acquisition order according to the modification of the second embodiment.

In the prior application described above, a position of the body motion is detected from the k-space data being imaged, and a synthesized signal is generated using the surrounding data to substitute for the data including the body motion. Since the body motion may have influence across the repetition time (TR), the odd-numbered measurement points and the even-numbered measurement points are measured by interleaved measurement as shown in FIG. 14A, so that the phase encoding is not adjacent to each other. In this case, either of the odd-numbered measurement points and the even-numbered measurement points, being acquired first, are set as the priority imaging data, and if the priority imaging data has been obtained by the time the imaging is aborted, image reconstruction by double-speed parallel imaging is performed.

Figure 14B:
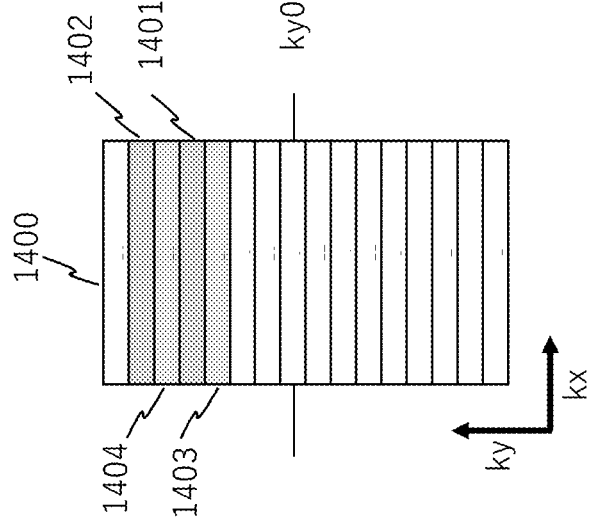

However, in the interleaved measurement method, assuming that body motion occurs at a certain phase encoded data items (e.g., 7th and 8th measurement data) 1401 and 1402, and the echo data 1401 is compensated (corrected) by using the adjacent data items (14th and 15th measurement data) 1403 and 1404, the data items 1403, 1404 are continuous in time-wise. Therefore, if the body motion occurs twice and there is an influence of body motion not only on the echo signal 1401, but also on the echo signals 1403 and 1404 on both sides used to compensate for the echo signal 1401, the compensation using the surrounding data may fail. Therefore, in order to more disperse the phase encoding, it is preferable to apply the imaging method that measures the position, not using the data acquisition order at every second position, but at every third position at least. For example, as shown in FIG. 14B, there is employed the data acquisition order at every third position. In this case, in the same manner as described above, even when the echo signals 1411, 1413 and 1414 become the data affected by the body motion, it is possible to disperse the influence of the body motion, since these data items are not stored continuously in the ky direction, thereby increasing a success rate of the body motion compensation.

In the example shown in FIG. 14B, since the data is acquired in the order at every third position, the measurement data items from the first to the sixth are set as the priority imaging data, whereby the image reconstruction by the parallel imaging at triple speed becomes possible, if the priority imaging data has been acquired by the time when the imaging is aborted.

Figure 15:
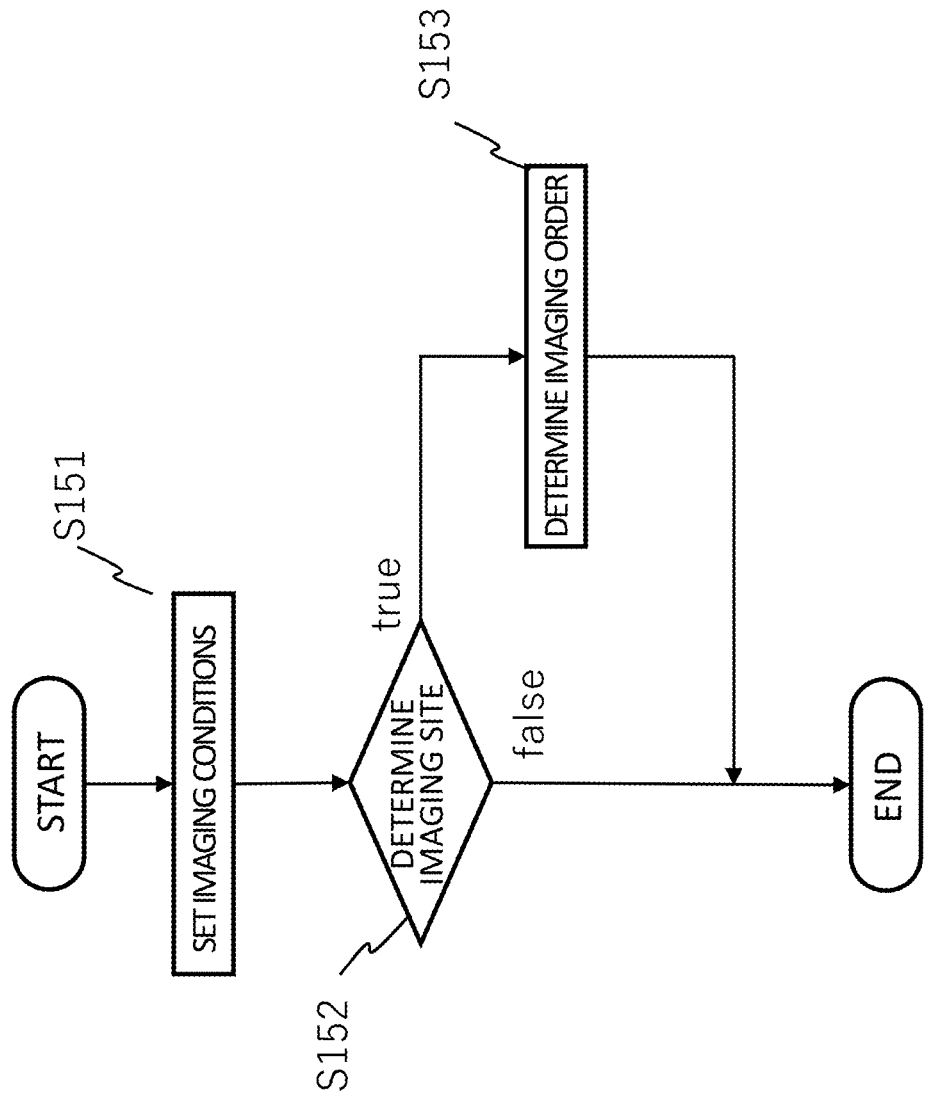
FIG. 15 is a flowchart showing the determination of the priority imaging data according to the modification of the second embodiment.

FIG. 15 shows the processing for determining the imaging order according to the present modification. First, imaging conditions are accepted via the input device 192 (UI) (S151). The imaging conditions include a selection of the function to compensate for the body motion and a designation of the imaging site. Initial settings of the function to compensate for the body motion include the measurement order according to the interleaving measurement method, for example. In S151, when the body motion compensation function is selected, the control unit 30 determines whether the imaging site is a site prone to body motion, based on the imaging site specified by the user (S152). A site where the body motion is liable to occur may be known empirically and registered in advance, or it may be specified by the user. If it is determined that the site is prone to the body motion, the imaging order is changed from the measurement order according to the interleaved measurement method set as default, to the order in which the measurement is performed at every third position or more sparse measurement points (S153).

When the imaging is started, the measurement of the k-space data is performed according to the set measurement order, and when the imaging is aborted, it is determined whether the measurement order is the default measurement order or the changed measurement order. Then, it is further determined whether the priority imaging data fixed by the measurement order has already been acquired, and if it has been acquired, image reconstruction by the parallel imaging is performed. That is, in the case of the measurement order as shown in FIG. 14A, the parallel imaging reconstruction of double speed is performed, using the first to the eighth echo data, and in the case of the measurement order as shown in FIG. 14B, the parallel imaging reconstruction of triple speed is performed, using the first to the sixth echo data.

Also in the present modification, the same technique may be applied not only to the 2D imaging, but also to the slice encoding direction of 3D imaging. It is also possible to use both the phase direction and the slice direction.

Third Embodiment

In the first and second embodiments, the image reconstruction method according to the fast-imaging method using the priority imaging data is parallel imaging. The present embodiment is directed to determination of the priority imaging data to be used for half-scan image reconstruction in the imaging using the FSE sequence.

The half-scan is a technique for performing image reconstruction by interpolating the data in the non-measurement area, using the data measured slightly more than half from the edge of k-space. There is known a method for reconstructing an image by using half-scan data when the imaging is aborted. As described in the second embodiment, in the FSE sequence, a plurality of echo signals simultaneously acquired with respect to the ky direction are arranged in a dispersed manner in k-space. Therefore, the k-space cannot be filled with the data sequentially from the edge, and thus this half-scan method is not applicable.

In the present embodiment, the k-space is divided into two areas and the measurement is performed for each of the areas separately, and this enables the image reconstruction using the half-scan data, when the imaging is aborted. Hereinafter, with reference to FIG. 16, there will be described a method for determining the priority imaging data and the measurement order according to the present embodiment.

Also in the present embodiment, when the image reconstructing function at the time of aborted imaging is selected as the imaging condition, the ratio of the half-scan is set initially. The ratio of the half-scan may be determined in advance in the system, or the user may provide the ratio. Further, as the ratio of the half-scan, the ratio of the priority imaging area or the ratio of the non-measurement area may be provided.

Next, at the ratio of the half-scan thus provided, the k-space is divided into two areas: the priority imaging area and the other area. That is, the number of shots of FSE is divided at the same ratio. For example, if the priority imaging area is ⅔ of the k-space, the remaining area is ⅓, and the number of shots is six, the data of the priority imaging area is collected by the first four shots, and the data of the remaining area is collected by the subsequent two shots. In addition, each of the areas is divided by the number of echo train into small regions. Signals (echo data) of the echo train measured by one shot are respectively arranged in the small regions obtained by dividing each area by the number of echo train. That is, in the small regions, there are arranged echoes of the same TE, respectively.

The order of collecting data in the small regions is determined so that an intensity difference between the echo data items adjacent in the ky direction is reduced, and the direction for collecting the echo data items (in the ky direction) is made different depending on the shot. Echo shift is a technique for shifting and storing the echoes so that the echo signal of the desired TE is located at the k-space center in the FSE sequence. At the time of the echo shift, when the echoes of the echo train are placed in the same direction in all the shots, the first echo and the last echo may become adjacent, and the intensity difference becomes large, causing artifacts such as ringing. In this embodiment, as described above, the direction for collecting the echo data varies depending on shots, whereby the intensity difference between adjacent echo data is reduced.

Figure 16:
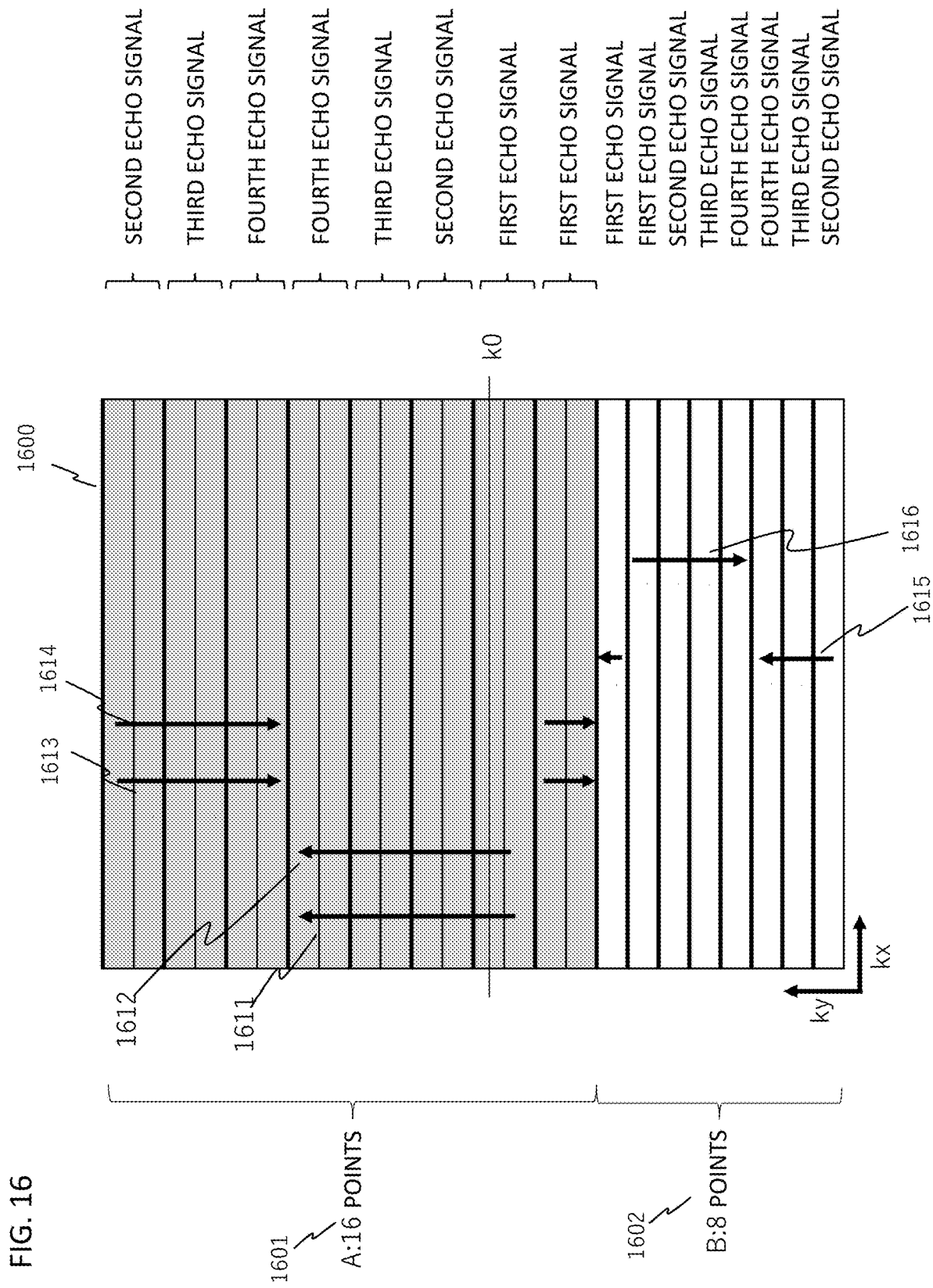
FIG. 16 illustrates an example of the signal acquisition order according to a third embodiment.

With reference to FIG. 16, a specific measurement order will be further described. In FIG. 16, as an example, the number of phase encoding is 24, the number of echo train is 4, and the ratio of the priority imaging area is 67% (⅔). At this rate, the area is divided into A area 1601 which will become the priority imaging area, and B area 1602. Since the number of shots is 6 (=phase encoding number 24/the number of echo train 4), the data in the priority imaging area 1601 is collected by 4 shots and the data in the B area 1602 is collected by 2 shots.

If the desired TE corresponds to the TE of the first echo signal, in the imaging of the priority imaging area 1601, data at the k-space center is acquired by the first echo, according to the first shot and the second shot (1611, 1612). The second to fourth echo data items are sequentially stored toward the upper side. Next, according to the third shot and the fourth shot (1613, 1614), the data items toward the lower side from the center of the k-space are acquired by the first echo, so that the signal intensity difference does not occur relative to the first shot (1611), and then the second to fourth echo data items are stored toward the center from the edge of k-space. Thus, all the neighboring echo data items correspond to the echo data of the same TE or the echo data of neighboring TEs.

Similarly, when acquiring data for the B area 1602, by the fifth shot (1615), a signal is acquired while shifting the first echo signal to be stored at the boundary with the A, so as not to cause a signal intensity difference relative to the A area. Then, by the sixth shot (1616), a signal is acquired so as not to cause a signal intensity difference relative to the fifth shot (1615). At this time, the order of the shots may be changed within the A area 1601, and within the B area 1602.

The processing of the image reconstruction is the same as the first embodiment (FIG. 7) except that the image reconstruction is performed according to the reconstruction technique where the half-scan estimation process is performed instead of the parallel imaging. That is, if the data for the priority imaging area A has been obtained by the time when scan imaging is aborted, estimation by the half-scan processing is performed for the non-measurement area to reconstruct an image.

In FIG. 16, there has been shown the case the echo for acquiring data of the k-space center is the first echo. This is also similar to the case of the echo shift for acquiring the k-space center by the second and following echoes. According to the ratio of the half scan, the k-space is divided into two areas, and the imaging order is determined such that the desired TE echo data is placed at k-space center. In this situation, the acquisition order may be made different so as to reduce the intensity difference between the echo data items.

Figure 17:
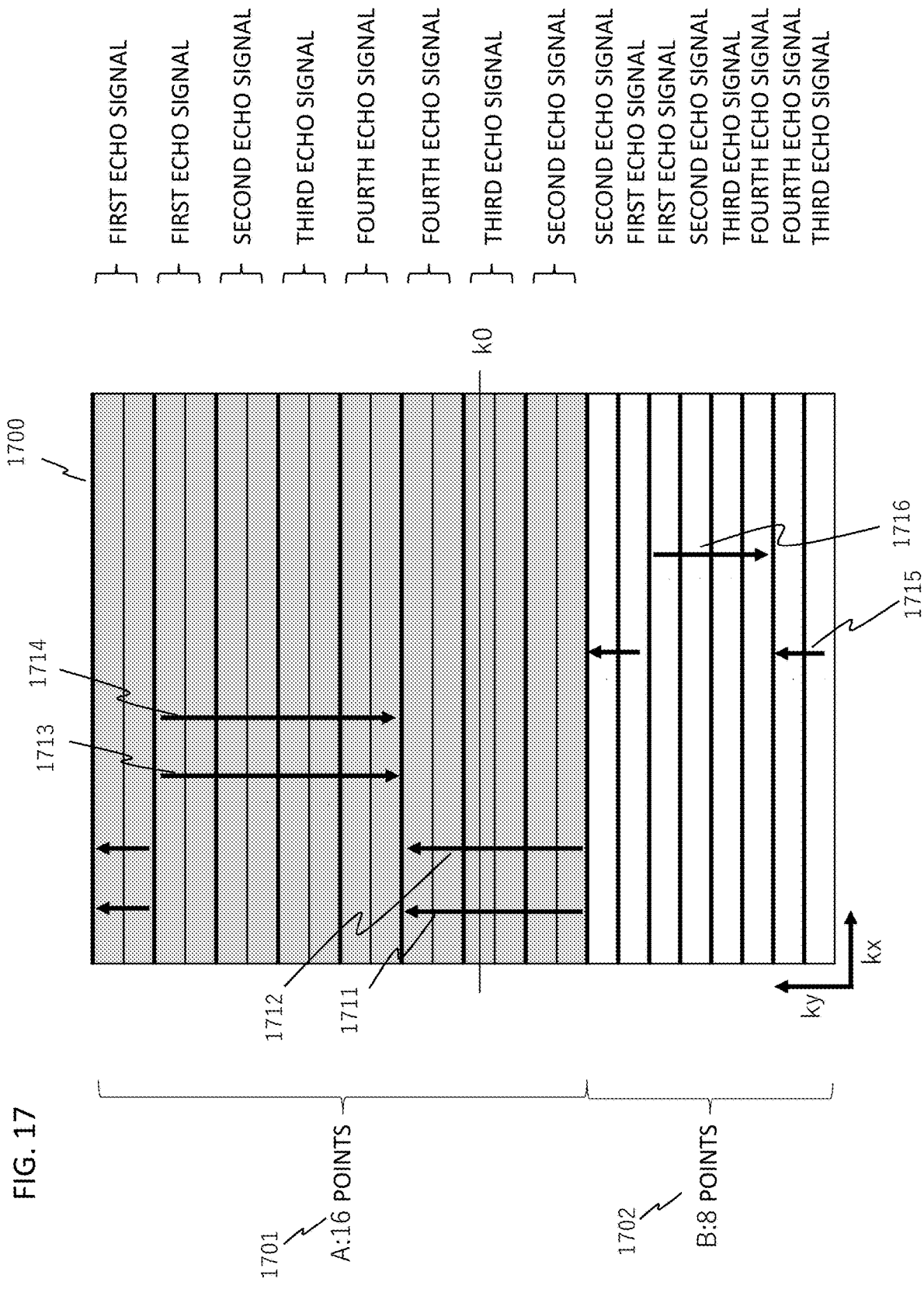
FIG. 17 illustrates another example of the signal acquisition order according to the third embodiment.

FIG. 17 shows the case where the TE of the third echo signal is the echo-shift TE. As in the case of FIG. 16, it is assumed the priority imaging area is ⅔ of the k-space 1700 and the other area is ⅓ thereof, the phase encoding number is 24, and the number of echo train is 4. In this case, the small region on the highest frequency side of the k-space is measured by the first echoes in the first two shots (1711, 1712) out of four shots for measuring the priority imaging area, and thereafter the regions including the k-space center are measured by the second to fourth echoes. By the remaining two shots (1713, 1714), the regions in the k-space, not measured in the first two shots, are measured. At that time, the order of measurement is set to the direction opposite to the first two shots. Thus, at the boundary between shots, the echoes with consecutive numbers will be made adjacent, and this eliminates the intensity difference between the echo data items.

The processing above is also applicable to the measurement of the area 1702, and the data of the area 1702 is measured by changing the directions between the fifth shot (1715) and the sixth shot (1716).

Fourth Embodiment (Including Radial Scanning)

Any of the first to the third embodiments and modifications thereof are directed to the case in which data of grid points in the k-space is measured axially (linear scan). In the present embodiment, the present invention is applied to the case where the imaging is performed by a method other than the measurement performed axially. Such imaging methods include non-orthogonal sampling methods, such as a radial scan for radially scanning the k-space, and a spiral scan for scanning the k-space spirally. There will now be described the present embodiment, taking as an example, the radial scan to which phase encoding is added.

Figure 18:
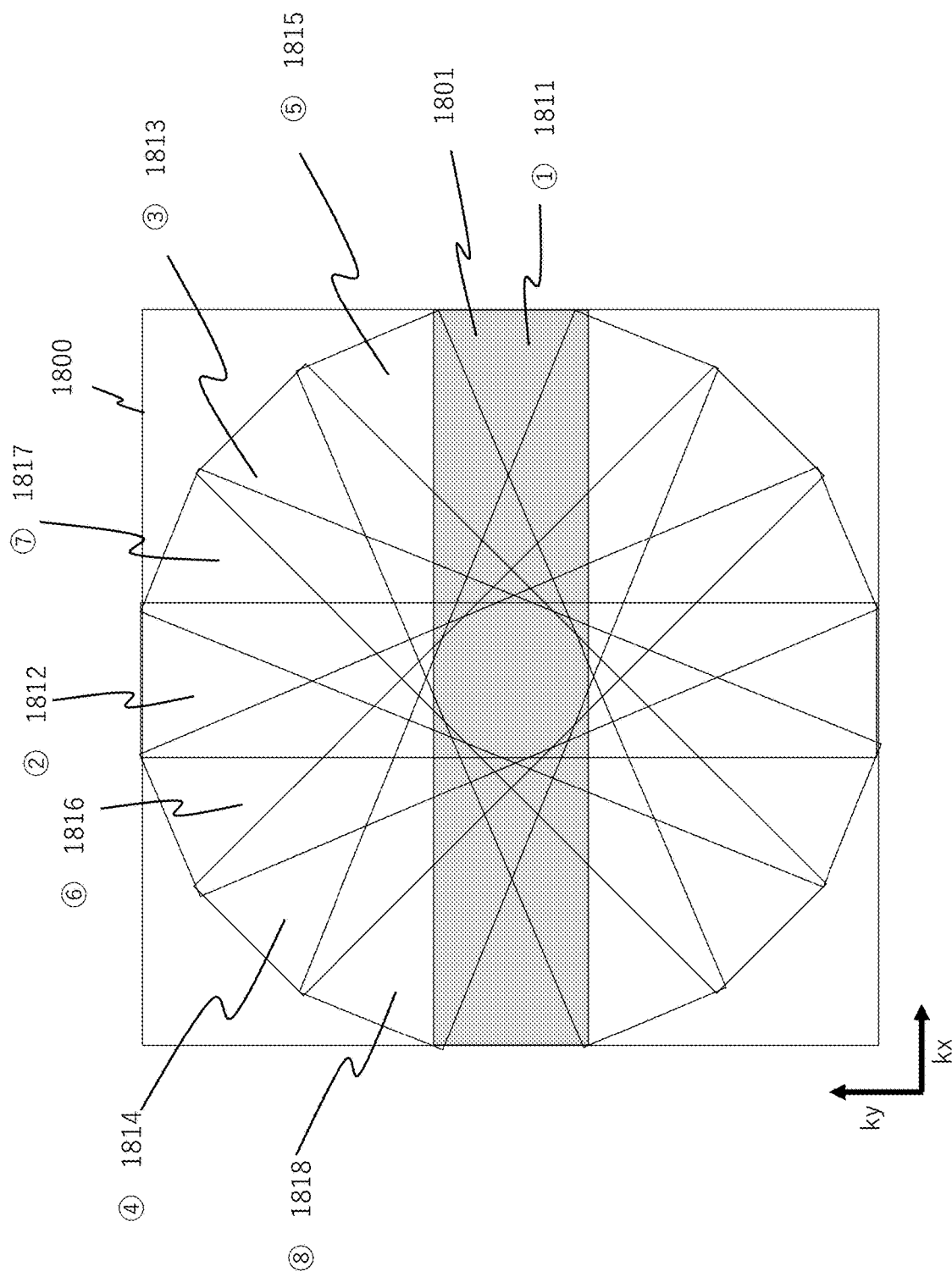
FIG. 18 illustrates an imaging method and the signal acquisition order according to a fourth embodiment.

As illustrated in FIG. 18, the radial scan is a measurement method for radially sampling the k-space 1800 on the kx-ky plane, to collect data while rotating an area, referred to as blade 1801 in which the phase encoding and the frequency encoding are orthogonal. As the basic order for collecting data, for example, the position parallel to the kx-axis is set as the first measurement area, and the blade is rotated sequentially in the left or right turn to collect the data in the circle inscribed in the k-space.

In the present embodiment, measurement is performed with changing the imaging order of the blade so that there is no data imbalance in the k-space when the imaging is aborted, for reconstructing an image using data at the time of aborted imaging. The imaging order of the blade may be determined to image the orthogonal position first, or may be determined so as to collect data evenly at an angle (about 137.5 degrees) which is a golden ratio. Alternatively, the data may be acquired in the order of imaging at every second blade. That is, the data defined as the priority imaging data is obtained at an angle being doubled with respect to the angle between the blades for data acquisition.

With reference to FIG. 18, there will be described an example of the image output function at the time when the imaging is aborted, according to the present embodiment. In FIG. 18, the numbers 1 to 8 enclosed in the circles provided next to the blades 1811 to 1818 at respective locations, represent the imaging order. In this example, when the k-space is acquired by eight blades, the position where the blade provided orthogonally is obtained first.

First, priority is given to the blades 1811 and 1812 orthogonal to the kx and ky axes. Any of the blades 1811 and 1812 may be acquired first. Since it is preferable the blade to be acquired next should not cause data imbalance in k-space, the blade 1813 angled at 45 degrees and the blade 1814 angled at 135 degrees are obtained in the present example. Any of these blades may be acquired first. Similarly for the remaining blades, the imaging is performed in the imaging order to acquire the blades 1815, 1816, 1817, and 1818, so as not to cause data imbalance in the k-space.

For the image reconstruction, when the imaging has acquired all the imaging data without aborted imaging, a normal image reconstruction is performed to output an image, and when the imaging is aborted, the image reconstruction is performed using the imaging data that has been obtained by the aborted point. In the image reconstruction according to the radial scan, data items at grid points in the k-space are interpolated from a plurality of measurement data located at positions close to the grid point, and then k-space data is created. Image reconstruction at the time of aborted imaging is basically the same, and the data items on the grid points not subjected to the measurement are interpolated from the measured data. The accuracy of the interpolation is lower relative to the case of measuring all the blades, but the image can be reconstructed by utilizing the measured data. In the other embodiments, when there is more measurement data than the priority imaging data, and the remaining data does not satisfy the next priority imaging data or all the imaging data, the remaining data is discarded. On the other hand, in the present embodiment, it is possible to utilize all the data measured so far, in order to determine the data of the grid point by interpolation. Therefore, once the imaging order is determined, the step of determining the status of the priority imaging data acquisition at the time of aborted imaging (S75 and others) as shown in FIG. 7 is not required. If there remains only too small amount of data at the time of aborted imaging, with respect to the blade to be acquired, this may cause lowering of the image quality, and thus a lower limit may be provided to the blade data.

In the present embodiment, there has been described the case where the imaging method is the radial scan with phase encoding, but it may be similarly applied to the radial scan without phase encoding. In this case, the minimum number of lines required for reconstruction is determined in advance, and the data items on the lines are set as the priority imaging data. If this priority imaging data has been collected by the time of the aborted imaging, the image reconstruction described above may be performed.

Fifth Embodiment

The present embodiment is directed to an image reconstruction method using the priority imaging data, according to iterative reconstruction such as compressed sensing (CS), instead of the parallel imaging.

Figure 19:
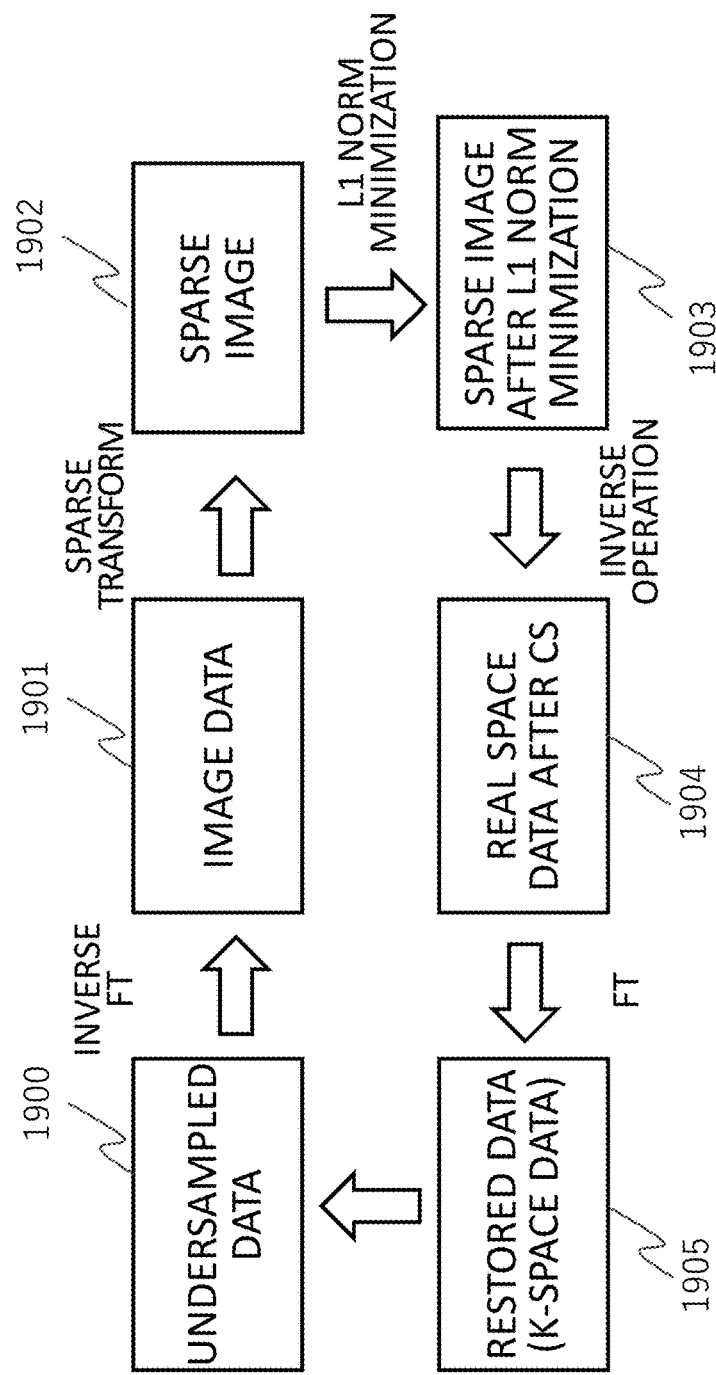
FIG. 19 illustrates image reconstruction according to a fifth embodiment.

The iterative reconstruction such as compressed sensing is an image reconstruction method utilizing data sparsity. As shown in FIG. 19, for example, undersampled data (measurement space data) 1900 is inputted, and after converting the data into image data 1901 according to inverse Fourier transform (inverse FT), followed by a sparse operation such as wavelet transform, and L1 norm minimization is performed on the sparse image 1902. The sparse image 1903 after the L1 norm minimization is returned to the real space data 1904, whose space is same as the image data 1901, by inverse operation, and rendered to be the k-space data 1905 by the Fourier transform. The same process is repeated using the k-space data 1905 as an input. According to such repetitive operation, it is possible to generate an image by restoring the original signals with high accuracy from a small amount of data.

It is known that in the iterative reconstruction such as the CS, the acceleration rate of the iterative reconstruction can be increased by using the imaging data with incoherence (randomness). In the present embodiment, as the priority imaging data, the imaging data having incoherence to be utilized for the iterative reconstruction such as the CS is preferentially collected. There are various techniques as the imaging method for ensuring incoherence suitable for iterative reconstruction. In here as an example, there will be described the case where radial sampling is performed using the golden angle with respect to the ky and kz axes.

Figure 20:
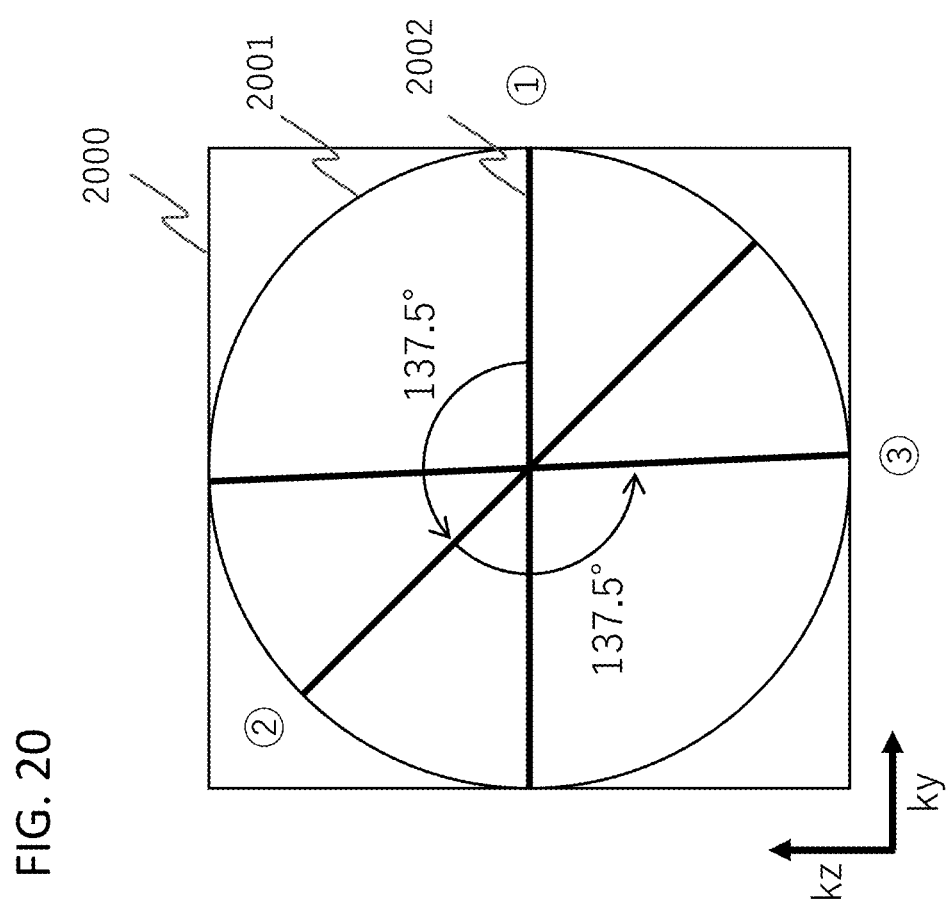
FIG. 20 illustrates the signal acquisition order according to the fifth embodiment.

As shown in FIG. 20, generally, in the radial sampling using the golden angle, in the region 2001 being the inscribed circle of the k-space 2000 on the ky, kz plane, the radial data acquisition line 2002 is rotated at a golden angle, and the imaging data on the line is acquired. If the imaging is not aborted, the data of all the measurement points is acquired by rotating at the golden angle, and normal image reconstruction is performed without iterative reconstruction, for example, by obtaining the data of the grid points of the k-space by interpolation from the data acquired radially. Then, after the matrix data is formed, the image reconstruction method by Fourier transform is executed. If the imaging is aborted, the image reconstruction by the repetitive operation such as the CS is performed by using the imaging data acquired so far. The acceleration rate at that time is the reciprocal of the ratio of the number of acquired data points to the total number of measurement points.

Alternatively, in the same manner as in the first embodiment, another method may be employed where the acceleration rate is determined in advance, the data of the measurement points having the number of data points satisfying the acceleration rate in the radial sampling is set as the priority imaging data, and after measuring the priority imaging data, the remaining measurement points are measured. In this case, if the priority imaging data has been acquired by the time of the aborted imaging, the image reconstruction is performed at the acceleration rate being provided, whereas if there is no aborted imaging, the normal image reconstruction is performed.

According to the present embodiment, as the method of image reconstruction, the iterative reconstruction such as the compressed sensing is used. Thus if the signal acquisition order is determined in a manner to provide the priority imaging data with high incoherence, it is possible to restore the image, even with a small amount of data that has been acquired by the aborted imaging, and the amount of data to be discarded can be reduced.

Modification of Fifth Embodiment

In the fifth embodiment, as the imaging method for acquiring imaging data having incoherence (randomness), the radial scan method is employed for collecting data with rotating the data acquisition line at a golden angle. On the other hand, in this modification, a spiral scan is used.

Figure 21A:
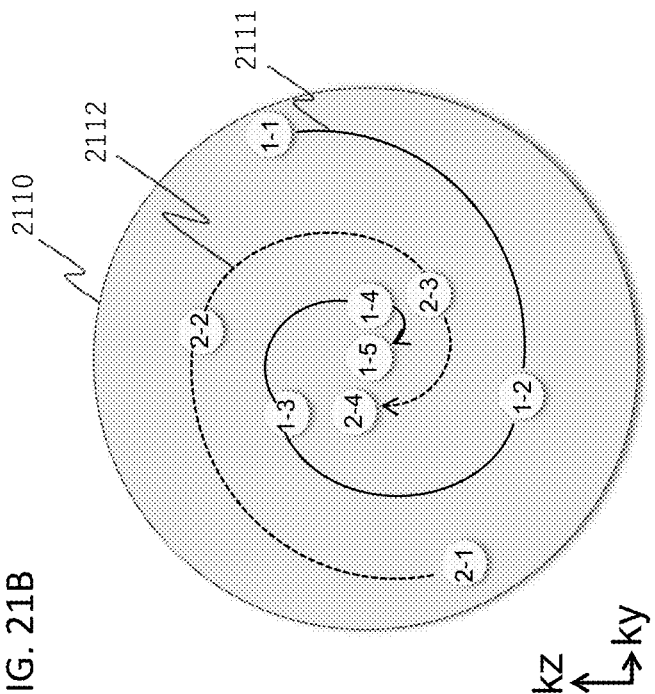
FIGS. 21A and 21B illustrate examples of the signal acquisition order according to the modification of the fifth embodiment.
Figure 21B:
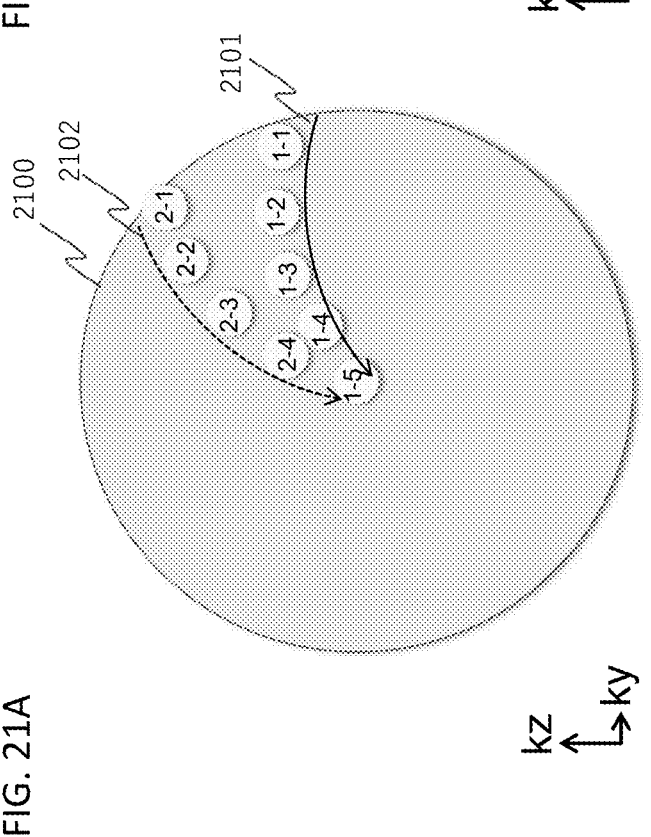

Examples of the priority imaging data and the signal acquisition order of this modification are shown in FIGS. 21A and 21B. In any of the examples, scanning (anti-centric scan) is performed toward the center spirally through the areas 2100 and 2110 in the circles inscribed in the k-space to collect the data. FIG. 21A shows that the data on the arcuate data acquiring line 2101 toward the center from the outside of the circle is acquired according to an imaging sequence for acquiring a plurality of echo signals in one shot, for example, by the FSE (Fast Spin Echo). Imaging is repeated while the data acquisition line is rotated, and the data of all k-space is collected by multiple shots. In the case of FIG. 21A, the way of rotation of the line is similar to the radial scan, and random data collection may also be possible by dispersing the angle between each shot.

If the data corresponding to a predetermined number of shots has already been collected by the time when the imaging is aborted, the image reconstruction is performed by the repetitive operation. A predetermined number of shots may be set in advance in the same manner as setting the R factor of the parallel imaging. Alternatively, the ratio of the number of shots with which data acquisition has been completed to the total number of shots is assumed as the reduction rate, and the repetitive operation may be performed using the reciprocal of the reduction rate as the R factor.

FIG. 21B collects the data of the entire k-space by a plurality of shots of EPI similarly to FIG. 21A, and the data acquisition lines 2111 and 2112 of each shot are spirals toward the k-space center from the outside of the inscribed circle 2110 of the k-space. Also in this case, the image reconstruction at the time of aborted imaging is the same as that of FIG. 21A. But as compared with FIG. 21A, the data obtained in each shot is randomly distributed in the k-space, so this provides more random data, even with a small amount of data, and thus achieving high accuracy of restoration by the iterative reconstruction.

What is claimed is:

1. A magnetic resonance imaging apparatus comprising:
a measuring unit including a static magnetic field generator, a gradient magnetic field generator, a radio frequency (RF) pulse transmitter, an RF signal receiver, and a sequencer;
a processor coupled to the measuring unit; and
a memory coupled to the processor, the memory storing instructions that when executed by the processor, configure the processor to:
control the measuring unit to collect k-space data made up of a plurality of nuclear magnetic resonance signals in accordance with a predetermined imaging method,
generate an image using the k-space data collected by the measuring unit,
determine as priority imaging data, imaging data that is available for image reconstruction according to a fast-imaging method, among the k-space data, and control a signal acquisition order of the signals in the k-space so that the measuring unit collects the priority imaging data in advance of other imaging data not included in the priority imaging data,
control the measuring unit to perform imaging such that the priority imaging data is measured first followed by measurement of remaining k-space data;
determine a signal acquisition status including whether collection of all the priority imaging data has been completed; and
perform image reconstruction using the priority imaging data upon determining signal acquisition is aborted and upon determining collection of all the priority imaging data has been completed.

2. The magnetic resonance imaging apparatus according to claim 1,
wherein the priority imaging data is the k-space data that is under-sampled according to a reduction factor of a parallel imaging method.

3. The magnetic resonance imaging apparatus according to claim 2,
wherein the priority imaging data is the k-space data obtained by under-sampling in one-dimensional direction of the k-space.

4. The magnetic resonance imaging apparatus according to claim 2, wherein the priority imaging data is the k-space data obtained by under-sampling in two-dimensional directions of the k-space.

5. The magnetic resonance imaging apparatus according to claim 4,
wherein the processor is configured to control the signal acquisition order so that the k-space data in a direction with a smaller number of data is collected in advance, out of the two-dimensional directions of the k-space.

6. The magnetic resonance imaging apparatus according to claim 2,
wherein the predetermined imaging method uses a fast spin-echo pulse sequence that divides the k-space into a plurality of regions, and collects the k-space data by sequentially changing the signal acquisition order so that signals of the same echo time are arranged in each of the regions, and
the processor is configured to control the signal acquisition order within each region so that the priority imaging data becomes the k-space data undersampled according to the reduction factor of the parallel imaging method.

7. The magnetic resonance imaging apparatus according to claim 6,
wherein the priority imaging data determiner determines as the priority data, data obtained by decimating the k-space data at every second position at least.

8. The magnetic resonance imaging apparatus according to claim 1,
wherein the predetermined imaging method uses a fast spin-echo pulse sequence that divides the k-space into a plurality of regions, and collects the k-space data by sequentially changing the signal acquisition order so that signals of the same echo time are arranged in each of the regions, and
wherein the processor is configured to set the priority imaging data that is available for half-scan reconstruction, in one of two areas obtained by dividing the k-space into two.

9. The magnetic resonance imaging apparatus according to claim 8,
wherein the processor is configured to divide and store echo trains respectively collected by a plurality of shots of the fast spin-echo pulse sequence, into the two areas, and perform control so that the signal acquisition order in each area is made different depending on the shot.

10. The magnetic resonance imaging apparatus according to claim 1,
wherein the predetermined imaging method is a radial scan sequence that collects the k-space data at a plurality of angles, along a radial direction of a circle inscribed in the k-space, and
wherein the processor is configured to determine data collected with changing the angle for data collection at a golden angle, as the priority imaging data.

11. The magnetic resonance imaging apparatus according to claim 10,
wherein the radial scan sequence includes a sequence for collecting blades of k-space data along the radial direction, at the golden angle.

12. The magnetic resonance imaging apparatus according to claim 10,
wherein the processor is configured to generate the image according to iterative reconstruction by using the priority imaging data.

13. The magnetic resonance imaging apparatus according to claim 1, further comprising:
a display coupled to the processor,
wherein the processor is configured to display the determined signal acquisition status on the display.

14. A method of controlling a magnetic resonance imaging apparatus comprising a processor coupled to a memory and a measuring unit including a static magnetic field generator, a gradient magnetic field generator, a radio frequency (RF) pulse transmitter, an RF signal receiver, and a sequencer, the method executed by the processor executing steps comprising:
controlling the measuring unit to collect via k-space data made up of a plurality of nuclear magnetic resonance signals in accordance with a predetermined imaging method;
generating an image using the collected k-space data; and
determining as priority imaging data, imaging data that is available for image reconstruction according to a fast-imaging method, among the k-space data, and controlling a signal acquisition order of the signals in the k-space so that the measuring unit collects the priority imaging data in advance of other imaging data not included in the priority imaging data;
controlling the measuring unit to perform imaging such that the priority imaging data is measured first followed by measurement of remaining k-space data; and
determining a signal acquisition status including whether collection of the priority imaging data has been completed; and
performing image reconstruction based on the fast-imaging method by using the priority imaging data, upon determining signal acquisition is aborted and upon determining collection of all the priority imaging data has been completed.

* * * * *